United States Patent [19]

Kamiya et al.

[11] 4,056,521
[45] Nov. 1, 1977

[54] PENAM AND CEPHAM DERIVATIVES AND PREPARATION THEREOF

[75] Inventors: Takashi Kamiya, Suita; Tsutomu Teraji; Masashi Hashimoto, both of Toyonaka; Osamu Nakaguti, Osaka; Teruo Oku, Kyoto, all of Japan

[73] Assignee: Fujisawa Pharmaceutical Co., Ltd., Osaka, Japan

[21] Appl. No.: 648,492

[22] Filed: Dec. 1, 1976

Related U.S. Application Data

[62] Division of Ser. No. 407,962, Oct. 19, 1973, Pat. No. 3,954,732.

[30] Foreign Application Priority Data

| Dec. 20, 1972 | Japan | 48-128658 |
| Dec. 20, 1972 | Japan | 48-128659 |
| Dec. 20, 1972 | Japan | 48-128660 |
| Dec. 21, 1972 | Japan | 48-128902 |
| Dec. 22, 1972 | Japan | 48-2270 |
| Dec. 23, 1972 | Japan | 48-1198 |
| Dec. 23, 1972 | Japan | 48-1201 |
| Aug. 1, 1973 | Japan | 47-87108 |

[51] Int. Cl.$^2$ .................................. C07D 499/44
[52] U.S. Cl. ........................................ 260/239.1
[58] Field of Search ............................ 260/239.1

[56] References Cited

U.S. PATENT DOCUMENTS 3,275,626  9/1966  Morin et al. .................. 260/243 C Primary Examiner—Gerald A. Schwartz
Attorney, Agent, or Firm—Oblon, Fisher, Spivak, McClelland & Maier

[57] ABSTRACT

Disclosed are antibacterial penicillins of the formula

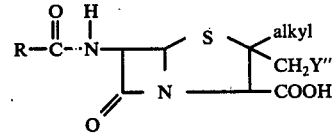

wherein Y" is a residue of a strong nucleophile and processes for preparing same.

6 Claims, No Drawings

PENAM AND CEPHAM DERIVATIVES AND PREPARATION THEREOF

This is a division of application Ser. No. 407,962, filed Oct. 19, 1973, now U.S. Pat. No. 3,954,732.

Having now generally described the invention, a further understanding can be attained by reference to certain specific examples which are provided herein for purposes of illustration only and are not intended to be construed as limiting unless otherwise so indicated.

Reaction of:

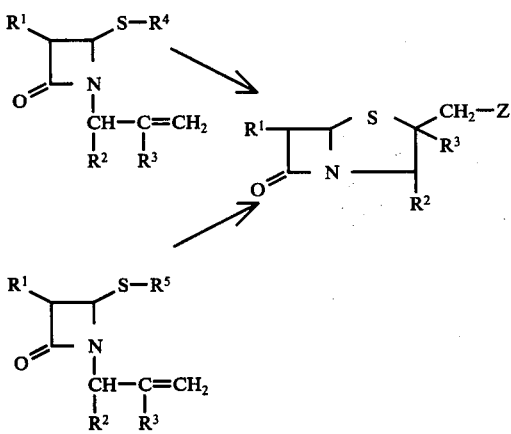

EXAMPLE 1

2,2,2-Trichloroethyl 2-oxo-3-(2-phenoxyacetamido)-4-(benzothiazol-2-yl)dithio-α-isopropenyl-1-azetidineacetate (0.65 g) was dissolved in chloroform (15 ml). To this solution was added cupric chloride (0.16 g) and then the mixture was stirred for 8 hours at room temperature. Precipitates were filtered off and the filtrate was washed with a saturated sodium bicarbonate aqueous solution and then with water and thereafter dried over magnesium sulfate. The solvent was distilled off to give oily 2,2,2,-trichloroethyl 2-chloromethyl-2-methyl-6-(2-phenoxyacetamido) penam-3-carboxylate (0.56 g).

Infrared Absorption Spectrum (Film): 3350, 1785, 1760 1685 cm$^{-1}$.

EXAMPLE 2

2,2,2-Trichloroethyl 2-oxo-3-(2-phenylacetamido)-4-(benzothiazol-2-yl)dithio-α-isopropenyl-1-azetidineacetate (0.63 g) was dissolved in chloroform (15 ml). To this solution was added cupric chloride (0.16 g) and then the mixture was stirred for 8 hours at room temperature. Precipitates were filtered off and the filtrate was washed with a saturated sodium bicarbonate aqueous solution and then with water and thereafter dried over magnesium sulfate. The crystals obtained by distilling off the solvent were washed with ether to give 2,2,2-trichloroethyl 2-chloromethyl-2-methyl-6-(2-phenylacetamido)penam-3-carboxylate (0.45 g), mp 108° to b 109° C.

Infrared Absorption Spectrum (Nujol): 3300, 1785, 1763, 1656 cm$^{-1}$.

EXAMPLE 3

2,2,2-Trichloroethyl 2-oxo-3-(2-phenylacetamido)-4-(benzothiazol-2-yl)dithio-α-isopropenyl-1-azetidineacetate (0.63 g) was dissolved in acetonitrile (12 ml). To this solution was added mercuric chloride (0.44 g) and then the mixture was stirred for 24 hours at room temperature. After the reaction, precipitates were filtered off and the filtrate was concentrated under reduced pressure and the obtained residue was dissolved in ethyl acetate. The ethyl acetate layer was washed with water, dried and the solvent was distilled off. The obtained residue was purified by chromatography on silica gel to give colorless needles of 2,2,2-trichloroethyl 2-chloromethyl-2-methyl-6-(2-phenylacetamido)penam-3-carboxylate (190 mg), mp 104° to 105° C, from the third and fourth fractions of fractions each of which was separated into 50 ml.

Infrared Absorption Spectrum (Nujol): 3300, 1785, 1763, 1656 cm$^{-1}$.

EXAMPLE 4

To a solution of methyl 2-oxo-3-(2-phenoxyacetamido)-4-anilinothio-α-isopropenyl-1-azetidineacetate (0.12 g), in dried methylene chloride (5 ml) was added 5% methanolic hydrochloric acid (0.8 ml) and the mixture was stirred for 10 hours at room temperature. After the reaction, methylene chloride was distilled off under reduced pressure from the reaction mixture. The residue was extracted with ethyl acetate and the extract was washed with water and dried. The solvent was distilled off to give oily methyl 2-chloromethyl-2-methyl-6-(2-phenoxyacetamido)-penam-3-carboxylate (0.085 g).

Infrared Absorption Spectrum (Chloroform): 3400, 1790, 1760, 1680 cm$^{-1}$.

EXAMPLE 5

There was obtained oily methyl 2-chloromethyl-2-methyl-6-(2-phenoxyacetamido)-penam-3-carboxylate (0.36 g) by treating in the similar manner as described in Example 4 using methyl 2-oxo-3-(2-phenoxyacetamido)-4-propylaminothio-α-isopropenyl-1-azetidineacetate (0.43 g).

The following compounds were obtained by using the same procedures as those of the Example 1. 2,2,2-Trichloroethyl 2-bromomethyl-2-methyl-6-(2-phenylacetamide)penam-3-carboxylate mp 90° to 93° C (dec.).
2. 2,2,2-Trichloroethyl 2-bromomethyl-2-methyl-6-[N-(2,2,2-trichloroethoxy)-carbonylphenylglycyl]-aminopenam-3-carboxylate (powder)
3. 2,2,2-Trichloroethyl 2-bromomethyl-2-methyl-6-(2-phenoxyacetamido)-penam-3-carboxylate (gummy).
4. 1-Cyclopropylethyl 2-bromomethyl-2-methyl-6-(2-phenylacetamido)-penam-3-carboxylate (oil).
5. 2,2,2-Trichloroethyl 2-bromomethyl-2-methyl-6-[2-(sydnon-3-yl) acetamido]penam-3-carboxylate (amorphous).
6. 2,2,2-Trichloroethyl 2-bromomethyl-2-methyl-6-[2-(4-hydroxyphenyl)-2-(1-cyclopropylethoxy)carbonyl-aminoacetamido]penam-3-carboxylate (powder).
7. 2,2,2-Trichloroethyl 2-bromomethyl-2-methyl-6-[2-(2-thienyl)acetamido]-penam-3-carboxylate (oil).
8. 3,5-Di-tert.-butyl-4-hydroxybenzyl-2-bromomethyl-2-methyl-6-(2-phenylacetamido)penam-3-carboxylate (white crystalline powder).
9. 2,2,2-Trichloroethyl 2-bromomethyl-2-methyl-6-[N-(1-cyclopropylethoxy)-carbonylphenylglycyl]-aminopenam-3-carboxylate (mp 130° to 135° C).

10. 2,2,2-Trichloroethyl 2-bromomethyl-2-methyl-6-(2-cyanoacetamido)-penam-3-carboxylate (amorphous).

Reaction of:

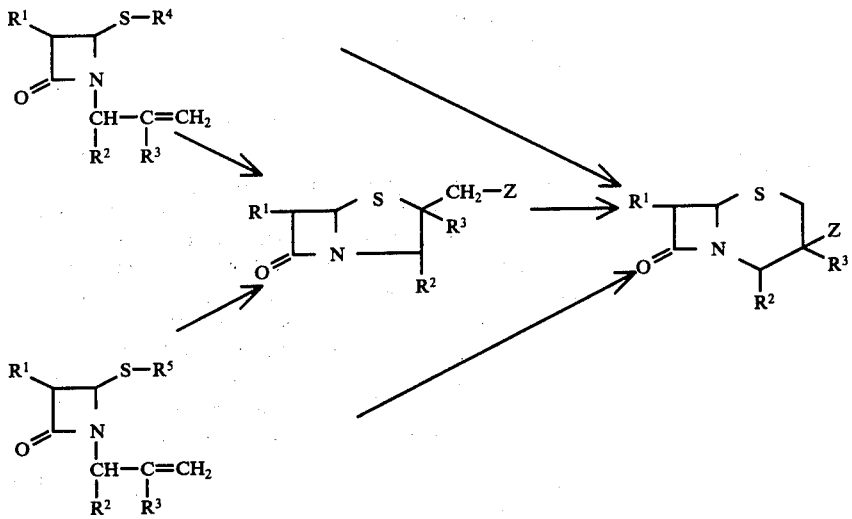

EXAMPLE 1

2,2,2-Trichloroethyl 2-oxo-3-(2-phenylacetamido)-4-(benzothiazol-2-yl)dithio-α-isopropenylazetidine-1-acetate (0.63 g) was dissolved in acetonitrile (12 ml). To this solution was added mercuric chloride (0.44 g) and the mixture was stirred for 24 hours at room temperature. After the reaction precipitates were filtered off and the filtrate was concentrated under reduced pressure. The obtained residue was dissolved in ethyl acetate and the ethyl acetate layer was washed with water and then dried. The solvent was distilled off and the obtained residue was purified by column chromatography on silica gel to give powdery 2,2,2-trichloroethyl 3-chloro-3-methyl-7-(2-phenylacetamido)cepham-4-carboxylate (70 mg) from the fifth and sixth fractions of fractions each of which was separated into 50 ml.

Infrared Absorption Spectrum (Nujol): 3400, 1775, 1760, 1675 cm$^{-1}$.

EXAMPLE 2

2,2,2-Trichloroethyl 2-oxo-3-(2-phenyl-acetamido)-4-(benzothiazol-2-yl)-dithio-α-isopropenylazetidine-1-acetate (1.26 g) was dissolved in methylene chloride (15 ml). To this solution was added dried zinc chloride (0.40 g) and the mixture was stirred for 2 days at room temperature. After the reaction, the reaction mixture was filtered and the filtrate was washed with sodium bicarbonate aqueous solution and then with water. The residue was subjected to column chromatography on silca gel (20 g) and eluted with chloroform. The third fraction of the fractions each of which was separated in about 30 ml was separated and the solvent was distilled off to give powdery 2,2,2-trichloroethyl 3-chloro-3-methyl-7-(2-phenylacetamido) cepham-4-carboxylate.

EXAMPLE 3

Methyl 2-oxo-3-(2-phenoxyacetamido)-4-anilinothio-α-isopropenylazetidine-1-acetate (0.12 g) was dissolved in dry methylene chloride (5 ml). To this solution was added 5% methanolic hydrochloric acid (0.8 ml) and the mixture was stirred for 10 hours at room temperature. After the reaction, the reaction mixture was concentrated under reduced pressure and the residue was extracted with ethyl acetate. The extract was washed with water and dried. The solvent was distilled off and the residue was subjected to column chromatography on silica gel using chloroform as developing solvent to give oily methyl 3-chloro-3-methyl-7-(2-phenoxyacetamido)cepham-4-carboxylate (0.07 g).

Infrared Absorption Spectrum (Chloroform): 3410, 1775, 1742, 1690 cm$^{-1}$.

EXAMPLE 4

Methyl 2-oxo-3-(2-phenoxyacetamido)-4-propylaminothio-α-isopropenylazetidine-1-acetate (0.43 g) was dissolved in dried methylene chloride. To this solution was added 5% methanolic hydrochloric acid (2 ml) and the mixture was stirred for 10 hours at room temperature. After the reaction, the reaction mixture was concentrated under reduced pressure and the residue was extracted with ethyl acetate. The extract was washed with water and dried. The solvent was distilled off and the residue was subjected to column chromatography on silica gel using chloroform as developing solvent to give oily methyl 3-chloro-3-methyl-7-(2-phenoxyacetamido)cepham-4-carboxylate (310 mg).

The following compounds were obtained by using the same procedures as those of the Examples 1 to 4.

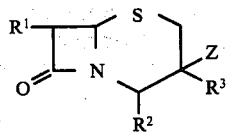

| No. | R¹ | R² | R³ | Z | Property of the product |
|---|---|---|---|---|---|
| 1 | ⌬—OCH₂CONH— | —COOCH₃ | —CH₃ | —Br | amorphous |
| 2 | ⌬—OCH₂CONH— | —COOCH₃ | —CH₃ | —I | oil |
| 3 | ⌬—OCH₂CONH— | —COOH | —CH₃ | —Br | amorphous |
| 4 | ⌬—CH₂CONH— | —COOCH₂CCp₃ | —CH₃ | —Br | mp 90 to 93° C (dec.) |
| 5 | NC—CH₂CONH— | —COOCH₂CCl₃ | —CH₃ | —Br | amorphous |
| 6 | [thienyl]—CH₂CONH— | —COOCH₂CCl₃ | —CH₃ | —Br | oil |

Reaction of:

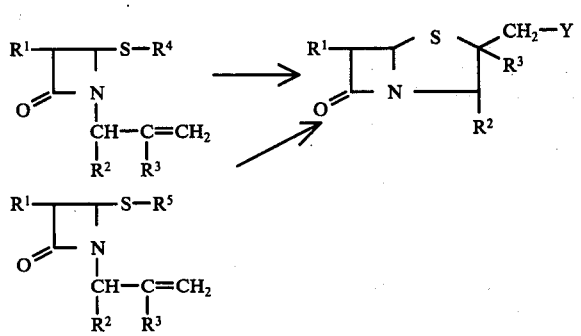

EXAMPLE 1

Methyl 2-oxo-3-(2-phenoxyacetamido)-4-(benzothiazol-2-yl)-dithio-α-isopropenyl-1-azetidine-acetate (1.06 g) and silver acetate (0.34 g) were suspended in tert-butanol and the mixture was refluxed for 48 hours. After the reaction, precipitates were filtered off and the filtrate was concentrated under reduced pressure. The residue was extracted with ethyl acetate. The ethyl acetate layer was washed with water, dried and the solvent was distilled off. The obtained residue was purified by column chromatography on silica gel using chloroform as developing solvent to give pale yellow oil of methyl 2-acetoxymethyl-2-methyl-6-(2-phenoxyacetamido)-penam-3-carboxylate (490 mg).

Infrared Absorption Spectrum (CHCl₃): 3410, 1792, 1745, 1740, 1690 cm⁻¹.

EXAMPLE 2

2,2,2-Trichloroethyl 2-oxo-3-(2-phenylacetamido)-4-(benzothiazol-2-yl)-dithio-α-isopropenyl-1-azetidine-acetate (0.63 g) was dissolved in chloroform (10 ml). To this solution was added lead tetraacetate (1.77 g) and the mixture was refluxed for 24 hours. To the reaction mixure was added water and precipitates were filtered off. The filtrate was separated into chloroform layer and aqueous layer and the aqueous layer was extracted with chloroform. The chloroform layer was combined, dried over magnesium sulfate and then the solvent was distilled off. The residue was prufied by column chromatography on silica gel using chloroform as developing solvent to give 2,2,2-trichloroethyl 2-acetoxymethyl-2-methyl-6-(2-phenylacetamido)-penam-3-carboxylate (0.11 g), mp 122° to 123° C.

EXAMPLE 3

2,2,2-Trichloroethyl 2-oxo-6-(2-phenylacetamido)-4-(benzothiazol-2-yl)dithio-α-isopropenyl-1-azetidineacetate (1.26 g) was dissolved in a mixture of chloroform (10 ml) and acetic acid (10 ml). To this solution was added lead tetraacetate (1.80 g) and the mixture was stirred for 7 hours at room temperature. Lead tetraacetate (1.80 g) was further added to this solution and the solution was stirred for 8 hours at 50° C. To the reaction mixture was added chloroform, and the solution was washed with a saturated sodium bicarbonate aqueous solution and then with water and thereafter dried over magnesium sulfate. The residue obtained by distilling off the solvent was purified by column chromatography on silica gel using chloroform as developing solvent to give 2,2,2-trichloroethyl 2-acetoxymethyl-2-methyl-6-(2- phenylacetamido)penam-3-carboxylate (0.26 g).

Infrared Absorption Spectrum (Nujol) 3280, 1792, 1748, 1660 cm$^{-1}$.

EXAMPLE 4

2,2,2-Trichloroethyl 2-oxo-3-[N-(1-cyclopropylethoxy)carbonylphenylglycy]-amino-4-(benzothiazol-2-yl)ditho-α-isopropenyl-1-azetidineacetate (1.52 g) was dissolved in dry methylene chloride (15 ) under ice-cooling. To this solution was dropwise added a solution of thiocyanogen (1m mole) in methylene chloride (10 ml) and the mixture was stirred for 24 hours at the same temperature. Precipitates were filtered off and the filtrate was washed with a saturated sodium bicarbonate aqueous solution and then with water. After drying over magnesium sulfate, the solvent was distilled off under reduced pressure to give oily 2,2,2-trichloroethyl 2-thiocyanatomethyl-2-methyl-6-[N- (1-cyclopropylethoxy)carbonylphenylglycyl]-aminopenam-3-carboxylate (1.3 g).

Infrared Absorption Spectrum (Film): 1780, 1765, 1680 cm$^{-1}$.

EXAMPLE 5

2,2,2-Trichloroethyl 2-oxo-3-(2-phenoxyacetamido)-4-(benzothiazol-2-yl)dithioα-isopropenyl-1-azetidineacetate (0.63 g) was dissolved in dried methylene chloride (10 ml) under ice-cooling. To this solution was dropwise added a solution of thiocyanogen (0.6 m mole) in methylene chloride (5 ml). After the mixtue was stirred for 24 hours at the same temperature, precipitates were filtered off. The filtrate was concentrated under reduced pressure and the residue was dissolved in ethyl acetate (10 ml). The ethyl acetate layer was washed with a saturated sodium bicarbonate aqueous solution and then with water and thereafter dried over magnesium sulfate. After the solvent was distilled off, the residue was crystallized by adding a small amount of ether. The crystals were filtered off and the filtrate was concentrated to give oily 2,2,2-trichloroethyl 2-thiocyanatomethyl-2-methyl6-(2-phenoxyacetamido)penam-3-carboxylate (0.49 g).

Infrared Absorption Spectrum (Film): 1785, 1760, 1690 cm$^{-1}$.

EXAMPLE 6

2,2,2-Trichloroethyl 2-oxo-3-(2-phenylacetamido)-4-(benzothiazol-2-yl)dithio-α-isopropenyl-1-azetidineacetate (5.04 g) was dissolved in dried methylene chloride (20 ml). To this solution was dropwise added a solution of thiocyanogen (4.5 m mole) in methylene chloride for 5 minutes under ice-cooling. After stirring for 7 hours at the same temperature, precipitates were filtered off. The filtrate was washed with a saturated sodium bicarbonate aqueous solution and then with warter and thereafter dried over magnesium sulfate. After distilling off the solvent under reduced pressure, the residue was crystallized by adding a small amount of ether to give 2,2,2-trichloroethyl 2-thiocyanatomethyl-2-methyl-6-(2-phenylacetamido)penam-3-carboxylate (3.58 g), mp 137° to 140° C.

EXAMPLE 7

2,2,2-Trichloroethyl 2-oxo-3-(2-phenylacetamido)-4-(benzothiazol-2-yl)dithio-α-isopropenyl-1-azetidineacetate (0.63 g) and potassium thiocyanate (150 mg) were dissolved in dried acetone (10 ml). To this solution was added p-toluenesulfonic acid monohydrate (0.19 g) and the mixture was stirred for 24 hours at room temperature. Precipitates were filtered off and the filtrate was concentrated under reduced pressure and then the residue was dissolved in ethyl acetate. The ethyl acetate layer was washed with a saturated sodium bicarbonate aqueous solution and then with water and thereafter dried over magnesium sulfate. The residue obtained by distilling off the solvent was crystallized by adding a small amount of ether to give 2,2,2-trichloroethyl 2-thiocyanatomethyl-2-methyl-6-(2-phenylacetamido)penam-3-carboxylate (330 mg).

EXAMPLE 8

2,2,2-Trichloroethyl 2-oxo-3-[3-(2-chlorophenyl)-5-methyl-isoxazol-4-carboxamido]-4-(benzothiazol-2-yl)dithio-α-isopropenyl-1-azetidineacetate (0.70 g) was dissolved in dried methylene chloride (10 ml) under ice-cooling. To this solution was dropwise added a solution of thiocyanogen (0.5m mole) in methylene chloride (5 ml) and the mixture was stirred for 24 hours at the same temperature. Precipitates were filtered off and the filtrate was washed with a saturated sodium bicarbonate aqueous solution and then with water and thereafter dried. The solvent was distilled off and the residue was pulverized by adding petroleum ether (about 10 ml) to give 2,2,2-trichloroethyl 2-thiocyanatomethyl-2-thiocyanatomethyl-2-methyl-6-[3-(2-chlorophenyl)-5-methylisoxazol-4-carboxamido]-penam-3-carboxylate (500 mg).

Infrared Absorption Spectrum (Nujol): 1785, 1770, 1670 cm$^{-1}$.

EXAMPLE 9

Acetic acid (5 ml) was added to a solution of 2,2,2-trichloroethyl 2-oxo-3-(2-phenylacetamido)-4-(benzothiazol-2-yl)dithio-α-isopropenyl-1-azetidineacetate (1.26 g) in ethyl acetate (15 ml) To this solution was added silver acetate (0.68 g) under stirring at room temperature and the mixture was stirred for 4 hours at the same temperature. After the reaction, precipitates was filtered off from the reaction mixture and the filtrate was washed with water, with 5% sodium bicarbonate aqueous solution and then filtered. The filtrate was washed with water, dried and the solvent was distilled off. The oily residue (0.87 g) was purified by thin layer chromatography and recrystallized from ether to give colorless needles of 2,2,2-trichloroethyl 2-acetoxymethyl-2-methyl-6-(2-phenylacetamido)penam-3-carboxylate, mp 116° to 118° C.

EXAMPLE 10

Methyl 2-oxo-3-(2-phenoxyacetamido)-4-anilinothio-α-isopropenyl-1-azetidineacetate (454 mg) was dissolved in methylene chloride (20 ml). To this solution were added methanol (5 ml) and then boron trifluoride etherate (0.124 g) under cooling at 0° C. The mixture was stirred for 3 hours at the same temperature and further stirred for 2 hours at 5° to 10° C. After the reaction, the reaction mixture was washed with 5% sodium bicarbonate aqueous solution and then with water, dried and the solvent was distilled off. The oily residue (25 g) was subjected to column chromatography on silica gel and eluted with chloroform. The eluate was separated into each 50 ml fraction and the seventh and eighth fractions were combined. The solvent was distilled off to give oily methyl 2-methoxymethyl-2-methy-6-(2-phenoxyacetamido)penam-3-carboxylate.

Infrared Absorption Spectrum (CHCl₃): 3370, 1787, 1742, 1685 cm⁻¹.

The following compounds were obtained by using the same procedures as those of the Example 1 to 10.

| No. | R¹ | R² | R³ | Y | Property of the product |
|---|---|---|---|---|---|
| 1 | C₆H₅-CH₂CONH- | -COOCH₂CCl₃ | -CH₃ | -N₃ | mp 105 to 106° C |
| 2 | C₆H₅-CH₂CONH- | -COOCH₂CCl₃ | CH₃ | -S-(1,3,4-thiadiazol-2-yl with 5-CH₃) | Oil. Infrared Absorption Spectrum (CHCl₃) 3320, 1790, 1765, 1680 cm⁻¹. |
| 3 | C₆H₅-CH₂CONH- | -COOCH₂CCl₃ | -CH₃ | -S-(benzothiazol-2-yl) | Oil. Infrared Absorption Spectrum (CHCl₃) 3400, 1790, 1765, 1680 cm⁻¹. |
| 4 | C₆H₅-CH₂CONH- | -COOCH₂CCl₃ | -CH₃ | -S-(1-methyl-1H-tetrazol-5-yl) | Oil. Infrared Absorption Spectrum (CHCl₃) 3300, 1790, 1765, 1680 cm⁻¹. |
| 5 | C₆H₅-CH₂CONH- | -COOCH₂CCl₃ | -CH₃ | -S-COCH₃ | Oil. Infrared Absorption Spectrum (CHCl₃) 3390, 1790, 1765, 1680 - 1690 cm⁻¹. |
| 6 | C₆H₅-CH₂CONH- | -COOCH₂CCl₃ | -CH₃ | -S-CS-N(piperidinyl) | Oil. Infrared Absorption Spectrum (CHCl₃) 3300, 1788, 1764, 1675 cm⁻¹ |
| 7 | C₆H₅-CH₂CONH- | -COOCH₂CCl₃ | -CH₃ | -S-(1-methyl-imidazol-2-yl) | Oil. Infrared Absorption Spectrum (CHCl₃) 3200, 1790, 1770, 1678 cm⁻¹ |
| 8 | C₆H₅-CH₂CONH- | -COOCH₂CCl₃ | -CH₃ | -S-(pyridin-4-yl) | Oil. Infrared Absorption Spectrum (Film) 3250, 1780, 1765, 1665 cm⁻¹ |
| 9 | C₆H₅-OCH₂CONH- | -COOCH₃ | -CH₃ | -S-(1,3,4-thiadiazol-2-yl with 5-CH₃) | Infrared Absorption Spectrum (Film) 3300, 1785, 1745, 1680 cm⁻¹ |
| 10 | C₆H₅-CH(NH-COOCH(CH₃)-cyclopropyl)CONH- | -COOCH₂CCl₃ | -CH₃ | -S-(1-methyl-1H-tetrazol-5-yl) | Oil. Infrared Absorption Spectrum (Film) 3270, 1780, 1760, 1710, 1680 cm⁻¹ |

-continued

| No. | R¹ | R² | R³ | Y | Property of the product |
|---|---|---|---|---|---|
| 11 | Ph-CH(NHCOOCH(CH₃)CH(CH₂)CH₂)-CHCONH— | —COOCH₂CCl₃ | —CH₃ | —S-(5-methyl-1,3,4-thiadiazol-2-yl) | Oil; Infrared Absorption Spectrum (Film) 3270, 1760, 1710, 1680 cm⁻¹ |
| 12 | C₆H₅CH₂CONH— | —COOCH₂CCl₃ | —CH₃ | —OCH₃ | Oil; Infrared Absorption Spectrum (CHCl₃) 3360, 1785, 1757, 1666 cm⁻¹ |
| 13 | C₆H₅OCH₂CONH— | —COOCH₃ | —CH₃ | —NHC₆H₅ | Oil; Infrared Absorption Spectrum (CHCl₃) 3410, 1785, 1748, 1690 cm⁻¹ |
| 14 | (1H-tetrazol-1-yl)CH₂CONH— | —COOCH₂CCl₃ | —CH₃ | —S-(1-methyl-1H-tetrazol-5-yl) | Amorphous; Infrared Absorption Spectrum (Nujol) 3220, 1780, 1760, 1700 cm⁻¹ |
| 15 | 3-(2-chlorophenyl)-5-methylisoxazol-4-yl-CONH— | —COOCH₂CCl₃ | —CH₃ | —S-(1-methyl-1H-tetrazol-5-yl) | Amorphous; Infrared Absorption Spectrum (Nujol) 3300, 1780, 1770, 1665 cm⁻¹ |
| 16 | H₂N— | —COOCH₂CCl₃ | —CH₃ | —SCN | toluenesulfonate mp 182 to 185° C (dec.) |
| 17 | C₆H₅CH₂CONH— | —COOH | —CH₃ | —SCOCH₃ | N,N'-dibenzyl-ethylenediamine salt mp 105 to 107° C |
| 18 | C₆H₅CH₂CONH— | —COOH | —CH₃ | —S—CS—N(piperidinyl) | N,N'-dibenzyl-ethylenediamine salt mp 100° C (dec.) |
| 19 | C₆H₅CH₂CONH— | —COOH | —CH₃ | —NHC₆H₅ | mp 120° C |
| 20 | 3-(2-chlorophenyl)-5-methylisoxazol-4-yl-CONH— | —COOH | —CH₃ | —S-(1-methyl-1H-tetrazol-5-yl) | N,N'-dibenzyl-ethylenediamine salt mp 117 to 119° C (dec.) |
| 21 | (1H-tetrazol-1-yl)CH₂CONH— | —COOH | —CH₃ | —S-(1-methyl-1H-tetrazol-5-yl) | mp 152 to 154° C |

-continued

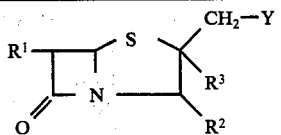

| No. | R¹ | R² | R³ | Y | Property of the product |
|---|---|---|---|---|---|
| 22 | ⌬—CH₂CONH— | —COOH | —CH₃ | $-S-\underset{\underset{CH_3}{N}}{\overset{N-N}{\diagup\!\!\!\diagdown}}$ | N,N'-dibenzyl-ethylenediamine salt mp 150 to 152° C (dec.) |
| 23 | ⌬—CH₂CONH— | —COOH | —CH₃ | benzimidazol-2-yl-N— | Sodium salt mp 200° C (dec.) |
| 24 | ⌬—CH₂CONH— | —COOH | —CH₃ | $-S-\underset{S}{\overset{N-N}{\diagup\!\!\!\diagdown}}-CH_3$ | Sodium salt mp 185 to 186° C (dec.) |

Reaction of:

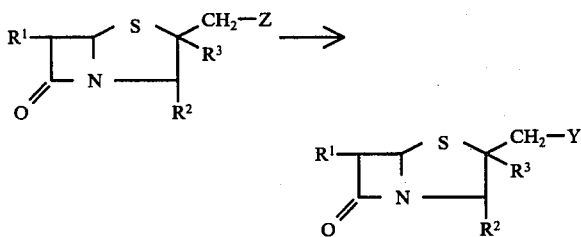

EXAMPLE 1

Potassium thiocyanate (1.17 g) was dissolved in a mixture of water (20 ml) and acetone (100 ml). To this solution was added 2,2,2-trichlorothyl 2-bromomethyl-2-methyl-6-(2-phenyl-acetamido) penam-3-carboxylate (5.45 g) at room temperature and the mixture was stirred for 5.5 hours at room temperature. After removing acetone under reduced pressure at room temperature, precipitates were collected by filtration, washed with water and further washed with ethanol to give 2,2,2-trichloroethyl 2-thiocyanatomethyl-2-methyl-6-(2-phenylacetamido)penam-3-carboxylate (4.10 g). This substance was recrystallized from isopropylether containing 5% acetone to give pure compound, mp 133° to 135° C.

Analysis for $C_{19}H_{18}N_3O_4S_2Cl_3$: Calc'd. : C43.64, H3.47, N8.04, S12.27, Cl 20.34. Found: : C43.84, H3.26, N7.99, S12.31, Cl20.31.

EXAMPLE 2

A mixture of 2,2,2-trichloroethyl 2-bromomethyl-b 2-methyl-6-(2-phenylacetamido)penam-3-carboxylate (1.08 g), sodium azide (0.26 g), acetone (20 ml) and water (4 ml) was stirred for 4 hours at room temperature. After removing acetone under reduced pressure, the residue was extracted with ethy acetate. The ethyl acetate layer was washed with water, with a saturated sodium bicarbonate queous solution and further with water and then dried over magnesium sulfate. The solvent was distilled off under reduced pressure and a small amount of ether was added to the residue. Precipitated crystals were filtered off and the solvent was distilled off from the filtrate. The crystalline residue was purified by column chromatography on silica gel using chloroform as developing solvent to give 2,2,2-trichloroethyl 2-azidomethyl-2-methyl-6-(2-phenylacetamido)penam-3-carboxylate (150 mg). This substance was crystallized by adding a small amount of a mixture of ether and petroleum ether and the crystals were recrystallized from ether to give pure compound, mp 105° to 106° C.

Analysis for $C_{18}H_{18}N_5O_4SCl_3$: Calc'd: C42.66, H3.58, N13.82, S6.33, Cl20.99. Found: C42.66, H3.40, H13.69, Cl20.74.

EXAMPLE 3

5-Methyl-1,3,4-thiadiazole-2-thiol (0.16 g) was dissolved in a mixture of pH 6.5 phosphate buffer (5 ml) and acetone (10 ml). To this solution was added 2,2,2-trichloroethyl 2-bromomethyl-2-methyl-6-(2-phenylacetamide)penam-3-carboxylate (0.54 g) and the mixture was stirred for 3 hours at room temperature. The reaction mixture was concentrated under reduced pressure and acetone was distilled off and thereafter the residue was extracted with ethyl acetate. The ethyl acetate layer was washed with sodium bicarbonate aqueous solution and then with water and thereafter dried over magnesium sulfate. The solvent was distilled off and the residue was purified by column chromatography on silica gel using chloroform as developing solvent to give oily 2,2,2-trichloroethyl 2-(5-methyl-1,3,4-thiadiazol-2-yl)thiomethyl-2-methyl-6-(2-phenylacetamido)-penam-3-carboxylate (0.09 g) from the second and third fractions each of which was separated into about 30 ml.

Infrared Absorption Spectrum (CHCl₃): 3320, 1790, 1765, 1680 cm⁻¹.

EXAMPLE 4

5-Methyl-1,3,4-thiadiazole-2-thiol (0.20 g) and sodium bicarbonate (0.85 g) were dissolved in formamide (7 ml). To this solution was added 2,2,2-trichloroethyl 2-bromomethyl-2-methyl-6-(2-phenylacetamido)- penam-3-carboxylate (0.54 g), and the mixture was stirred for 5 hours at room temperature. To the reaction mixture was added water, and the mixture was extracted with ethyl acetate. The ethyl acetate layer was washed with a saturated sodium bicarbonate aqueous solution and then with water and thereafter dried over magnesium sulfate. The residue obtained by distilling off the solvent was purified by column chromatography on silica gel using chloroform as developing solvent to give oily 2,2,2-trichloroethyl 2-(5-methyl-1,3,4-thiadiazol-2-yl)thiomethyl-2-methyl-6-(2-phenylacetamido)penam-3-carboxylate (0.20 g) from the third fractions each of which was separated into about 30 ml.

EXAMPLE 5

Benzothiazole-2-thiol (0.20 g) was dissolved in a mixture of pH 6.7 phosphate buffer (15 ml) and dioxane (15 ml). To this solution was added 2,2,2-trichloroethyl 2-bromomethyl-2-methyl-6-(2-phenylacetamido)penam-3-carboxylate (0.54 g) and the mixture was stirred for 7 hours at room temperature. After the reaction was completed, dioxane was distilled off and the residue was extracted with ethyl acetate. The ethyl acetate layer was washed with a 2% potassium carbonate aqueous solution and then with water and thereafter dried over magnesium sulfate. The residue obtained by distilling off the solvent was purified by column chromatography on silica gel using chloroform as developing solvent to give oily 2,2,2-trichloroethyl2-(benzothiazol-2-yl)thiomethyl-2-methyl-6-(2-phenylacetamido)penam-3-carboxylate (0.15 g) from the second fraction of fractions each of which was separated into 30 ml.

Infrared Absorption Spectrum (CHCl$_3$). 3400, 1790, 1765, 1680 cm$^{-1}$.

EXAMPLE 6

To a solution of 1-methyl-1H-tetrazole-5-thiol (0.23 g) in a mixture of pH 6.9 phosphate buffer (15 ml) and acetone (20 ml) was added 2,2,2-trichloroethyl 2-bromomethyl-2-methyl-6-(2-phenylacetamido)penam-3-carboxylate (0.54 g), and the mixture was stirred for 5 hours at room temperature. Acetone was distilled off from the reaction mixture. The aqueous layer was extracted with ethyl acetate and the extract was washed with sodium bicarbonate aqueous solution and then with a saturated sodium chloride aqueous solution. After the extract was dried over magnesium sulfate, the solvent was distilled off. The residue was purified by column chromatography on silica gel to give oily 2,2,2-trichloroethyl 2-(1-methyl-1H-tetrazol-5-yl)-thiomethyl-2-methyl-6-(2-phenylacetamido) penam-3-carboxylate (0.27 g).

Infrared Absorption Spectrum (CHCl$_3$). 3300, 1790, 1765, 1680 cm$^{-1}$.

EXAMPLE 7

Acetone (20 ml) and thioacetic acid (0.12 g) were added to pH 6.7 phosphate buffer (20 ml). To a mixture was added 2,2,2-trichloroethyl 2-bromomethyl-2-methyl-6-(2-phenylacetamido)penam-3-carboxylate (0.54 g) under stirring. After stirring for 5 hours at room temperature, the reaction mixture was post-treated in the similar manner as described in Example 6 to give oily 2,2,2-trichloroethyl 2-acetylthiomethyl-2-methyl-6-(2-phenylacetamido)penam-3-carboxylate (0.173 g).

Infrared Absorption Spectrum (CHCl$_3$): 3390, 1790, 1965, 1690 ~ 1685 cm$^{-1}$.

EXAMPLE 8

Sodium piperidine-1-dithiocarboxylate (0.37 g) was dissolved in a mixture of pH 6.7 phosphate buffer (20 ml) and acetone (25 ml) and then to this solution was added 2,2,2-trichloroethyl 2-bromomethyl-2-methyl-6-(2-phenylacetamido)penam-3-carboxylate (0.54 g). After stirring for 3 hours at room temperature, the reaction mixture was post-treated in the similar manner as described in Example 6 to give oily 2,2,2-trichloroethyl 2-piperidinothiocarbonyl-thiomethyl-2-methyl-6-(2-phenylacetamido)penam-3-carboxylate (0.11 g).

Infrared Absorption Spectrum (CHCl$_3$): 3300, 1788, 1764, 1675 cm$^{-1}$.

EXAMPLE 9

Acetone (25 ml) was added to a solution of 1-methylimidazole-2-thiol (0.23 g) in pH 6.9 phosphate buffer (20 ml). To this solution was added 2,2,2-trichloroethyl 2-bromomethyl-2-methyl-6-(2-phenylacetamido)penam-3-carboxylate (0.54 g), and the mixture was stirred for 3 hours at room temperature.

The reaction mixture was post-treated in the similar manner as described in Example 6 to give oily 2,2,2-trichloroethyl 2-(1-methylimidazol-2-yl)thiomethyl-2-methyl-6-(2-phenylacetamido)penam-3-carboxylate (0.29 g).

Infrared Absorption Spectrum (CHCl$_3$): 3200, 1790, 1770, 1678 cm$^{-1}$.

EXAMPLE 10

Acetone (25 ml) was added to a solution of pyridine-4-thiol (0.22 g) in pH 6.8 phosphate buffer (20 ml). To this solution was added 2,2,2-trichloroethyl 2-bromomethyl-2-methyl-6-(2-phenylacetamido)penam-3-carboxylate (0.54 g), and the mixture was stirred for 3 hours at room temperature.

The reaction mixture was post-treated in the similar manner as described in Example 6 to give oily 2,2,2-trichloroethyl 2-(4-pyridyl)-thiomethyl-2-methyl-6-(2-phenylacetamido)penam-3-carboxylate (0.15 g).

Infrared Absorption Spectrum (Film): 3250, 1780, 1765, 1665 cm$^{-1}$.

EXAMPLE 11

5-Methyl-1,3,4-thiadiazole-2-thiol (0.4 g) was dissolved in a mixture of pH 7.3 phosphate buffer (20 ml) and acetone (20 ml). To this solution was added a solution of methyl 2-bromomethyl-2-methyl-6-(2-phenoxyacetamido)penam-3-carboxylate (0.80 g) in acetone (10 ml) and the mixture was stirred for 4 hours at room temperature. After the reaction was completed, acetone was distilled off from the reaction mixture and the residue was extracted with ethyl acetate. The extract was washed with sodium bicarbonate aqueous solution and then with water and thereafter dried over magnesium sulfate. The solvent was distilled off and the residue was subjected to column chromatography on silica gel (60 g) and eluted with chloroform. The eluate was separated into fractions of each about 30 ml to give methyl 2-(5-methyl-1,3,4-thiadiazol-2-yl)thiomethyl-2-methyl-6-(2-phenoxyacetamido)penam-3-carboxylate (0.28 g) from the fourth to seventh fractions.

Infrared Absorption Spectrum (Film): 3300, 1785, 1745, 1690 cm$^{-1}$.

EXAMPLE 12

Acetic acid (2 ml) was added to a solution of 2,2,2-trichloroethyl 2-bromomethyl-2-methyl-6-(2-phenylacetamido)penam-3-carboxylate (0.54 g) in methylene chloride (10 ml). And to this solution was added silver acetate (0.34 g) water stirring at room temperature and then the mixture was stirred for 2.5 hours. After the reaction was completed, the reaction mixture was filtered under reduced pressure and the filtrate was washed with 5% hydrochloric acid and then filtered again. The oily residue was crystallized by treating with ether and the crystals were collected by filtration and then dried to give colorless needles of 2,2,2-trichloroethyl-2-acetoxymethyl-2-methyl-6-(2-phenylacetamido)-penam-3-carboxylate (0.21 g), mp 116° to 118° C.

EXAMPLE 13

A solution of 2,2,2-trichloroethyl 2-bromomethyl-2-methyl-6-[N-(1-cyclopropylethoxy)carbonylphenylglycyl]-aminopenam-3-carboxylate (6.75 g) in acetone (50 ml) was added to a solution of 1-methyl-1H-tetramole-5-thiol (2.6 g) in a mixture of phosphate buffer (200 ml) and acetone (200 ml), under cooling at 5° C, and the mixture was stirred for 5 hours at the same temperature. After the reaction was completed, acetone was distilled off from the reaction mixture under reduced pressure and the residue was extracted with ethyl acetate. The extract was washed with 5% sodium bicarbonate aqueous solution and then with water, dried. The solvent was distilled off. The oily residue was subjected to column chromatography on silica gel (180 g) and eluted with chloroform. The eluate was separated into fractions of each 50 ml and after collecting the fractions of the eleventh to sixteenth, the solvent was distilled off to give oily 2,2,2-trichloroethyl 2-(1-methyl-1H-tetrazol-5-yl) thiomethyl-2-methyl-6-[N-(1-cyclopropylethoxy)carbonylphenylglycyl] aminopenam-3-carboxylate (3.15 g).

Infrared Absorption Spectrum (Film): 3270, 1780, 1760, 1710, 1680 cm$^{-1}$.

EXAMPLE 14

By treating in the similar manner as described in Example 13 using 2,2,2-trichloroethyl 2-bromomethyl-2-methyl-6-[N-(1-cyclopropylethoxy)carbonylphenylglycyl]aminopenam-3-carboxylate (6.72 g), 5-methyl-1,3,4-thiadiazole-2-thiol (1.98 g), pH 6.8 phosphate buffer (200 ml) and acetone (250 ml), there was obtained oily 2,2,2-trichloroethyl 2-(5-methyl-1,3,4-thiadiazol-2-yl)-thiomethyl-2-methyl-6-[N-(1-cyclopropylethoxy)-carbonylphenylglycyl]aminopenam-3-carboxylate (1.16 g).

Infrared Absorption Spectrum (CHCl$_3$): 3420, 1790, 1770, 1708, 1687 cm$^{-1}$.

EXAMPLE 15

A solution of 2,2,2-trichloroethyl 2-bromomethyl-2-methyl-6-[N-(1-cyclopropylethoxy)carbonylphenylglycyl]aminopenam-3-carboxylate (3.6 g) in formamide (40 ml) was added to a solution of sodium bicarbonate (0.66 g) and 5-methyl-1,3,4-thiadiazole-2-thiol (1.1 g) in formamide (60 ml) under ice-cooling, after which the mixture was stirred for 4.5 hours at the same temperature. After the reaction was completed, the reaction mixture was poured into water and extracted with ethyl acetate. The extract was washed with 5% sodium bicarbonate aqueous solution and then with water, dried, after which the solvent was distilled off. The oily residue was subjected to column chromatography on silica gel (110 g) and eluted with chloroform. The eluate was separated into fractions of each 50 ml and after collecting the fractions of the fifteenth and sixteenth. the solvent was distilled off to give oily 2,2,2-trichloroethyl 2-(5-methyl-1,3-thiadiazol-2-yl)thiomethyl-2-methyl-6-[N-(1-cyclopropylethoxy)carbonylphenylglycyl]-aminopenam-3-carboxylate (0.-2 g).

EXAMPLE 16

2,2,2-trichloroethyl 2-bromomethyl-2-methyl-6-(2-phenylacetamido)penam-3-carboxylate (1.10 g) dissolved in methylene chloride (15 ml). To this solution was added aniline (0.28 g) under cooling at −10° C and then silver fluoroborate (0.-3 g), after which the mixture was stirred for 2 hours. After the reaction was completed, the reaction mixture was washed with a dilute phosphoric acid aqueous solution and then with water, dried over magnesium sulfate, after which the solvent was distilled off. The residue was subjected to column chromatography at silica gel (20 g) and eluted with chloroform. The eluate was separated into fractions of each about 20 ml. The second to seventh fractions were collected and the solvent was distilled off to give 2,2,2-trichloroethyl 2-anilinomethyl-2-methyl-6-(2-phenylacetamido)-penam-3-carboxylate (0.8- g), mp 148° to 149° C.

Infrared Absorption Spectrum (CHCl$_3$): 3400, 1780, 1765, 1680 cm$^{-1}$.

EXAMPLE 17

By treating in the similar manner as described in Example 16 using methyl 2-bromomethyl-2-methyl-6-(2-phenoxyacetamido)penam-3-carboxylate (0.88 g), aniline (0.28 g), silver fluoroborate (0.43 g) and methylene chloride (15 ml), there was obtained oily methyl 2-anilinomethyl-2-methyl-6-(2-phenoxyacetamido)-penam-3-carboxylate (0.41 g) from the fractions of the third to seventh.

Infrared Absorption Spectrum (CHCl$_3$); 3410, 1785, 1748, 1690 cm$^{-1}$.

EXAMPLE 18

2,2,2-Trichloroethyl 2-bromomethyl-2-methyl-6-(2-phenylacetamido)-penam-3-carboxylate (1.10 g) was dissolved in methylene chloride (12 ml) and to this solution was added methanol (3 ml). And to the solution was added silver fluoroborate (0.45 g) under stirring under cooling at −10° C and the mixture was stirred for 2 hours at the same temperature. After the reaction was completed, the reaction mixture was filtered and the filtrate was washed with sodium bicarbonate aqueous solution and then with water, dried over magnesium sulfate and thereafter concentrated. The residue was subjected to column chromatography on silica gel (25 g) and eluted with chloroform. The eluate was seprated into fractions of about 20 ml and the first and second fractions were collected. After distilling off the solvent, the residue was dried to give oily 2,2,2-trichloroethyl 2-methoxymethyl-2-methyl-6-(2-phenylacetamido)penam-3-carboxylate.

Infrared Absorption Spectrum (CHCl$_3$); 3360, 1785, 1757, 1666 cm$^{-1}$.

EXAMPLE 19

By treating in the similar manner as described in Example 18 using methyl 2-bromomethyl-2-methyl-6-(2-phenoxyacetamido)penam-3-carboxylate instead of 2,2,2-trichloroethyl 2-bromomethyl-2-methyl-6-(2-phenylacetamido)penam-3-carboxylate, there was obtained oily methyl 2-methoxymethyl-2-methyl-6-(2-phenoxyacetamido)penam-3-carboxylate.

Infrared Absorption Spectrum (CHCl$_3$) 3370, 1787, 1742, 1685 cm$^{-1}$.

EXAMPLE 20

By treating the similar manner as described in Example 11 using 2,2,2-trichloroethyl 2-bromomethyl-2-methyl-6-[3-(2-chlorophenyl)-5-methylisoxazole-4-carboxamino]penam-3-carboxylate and 1-methyl-IH-tetrazole-5-thiol in a mixture of pH 6.85 phosphate buffer and acetone, there was obtained amorphous 2,2,2-trichloroethyl 2-(1-methyl-IH-tetrazol-5-yl)thiomethyl-2-methyl-6-[3-(2-chlorophenyl)-5-methylisoxazole-4-carboxamido]penam-3-carboxylate.

Infrared Absorption Spectrum (Nujol); 3300, 1780, 1770, 1665 cm$^{-1}$.

EXAMPLE 21

By treating in the similar manner as described in Example 11 using 2,2,2-trichloroethyl 2-bromomethyl-2-methyl-6-[2-(1H-tetrazol-1-yl)-acetamido]penam-3-carboxylate and 1-methyl-IH-tetrazole-5-thiol in a mixture of pH 6.85 phosphate buffer and acetone, there was obtained amorphous 2,2,2-trichloroethyl-2-(1-methyl-1H-tetrazol-5-yl)thiomethyl-2-methyl-6-[2-(1H-tetrazol-1-yl)acetamido]penam-3-carboxylate.

Infrared Absorption Spectrum (Nujol) 3220, 1780, 1760, 1700 cm$^{-1}$.

| No. | R$^1$ | R$^2$ | R$^3$ | Y | Property of the products |
|---|---|---|---|---|---|
| 1 | phenyl-OCH$_2$CONH— | —COOCH$_2$CCl$_3$ | —CH$_3$ | —SCN | Oil<br>Infrared Absorption Spectrum (Film) 1785, 1760, 1690 cm$^{-1}$. |
| 2 | phenyl-CHCONH—, NHCOCHCH$_3$, cyclopropyl | —COOCH$_2$CCl$_3$ | —CH$_3$ | —SCN | Oil<br>Infrared Absorption Spectrum (Film) 1780, 1765, 1680 cm$^{-1}$. |
| 3 | 2-chlorophenyl-isoxazole-CONH—, CH$_3$ | —COOCH$_2$CCl$_3$ | —CH$_3$ | —SCN | Powder<br>Infrared Absorption Spectrum (Nujol) 1785, 1770, 1670 cm$^{-1}$. |
| 4 | H$_2$N— | —COOCH$_2$CCl$_3$ | —CH$_3$ | —SCN | toluenesulfanate<br>mp 182 to 185° C (dec.) |
| 5 | phenyl-CH$_2$CONH— | —COOH | —CH$_3$ | —SCOCH$_3$ | N,N'-dibenzylethylenediamine salt<br>mp 105 to 107° C |
| 6 | phenyl-CH$_2$CONH— | —COOH | —CH$_3$ | —S—CS—N(piperidine) | N,N'-dibenzylethylenediamine salt<br>mp 100° C (dec.) |
| 7 | phenyl-CH$_2$CONH— | —COOH | —CH$_3$ | —NH-phenyl | mp 120° C |
| 8 | 2-chlorophenyl-isoxazole-CONH—, CH$_3$ | —COOH | —CH$_3$ | —S-tetrazolyl-N-CH$_3$ | N,N'-dibenzylethylenediamine salt<br>mp 117 to 119° C (dec.) |

-continued structure:
$$R^1\text{—}\underset{O}{\overset{\phantom{|}}{\bigsqcup}}\text{—N—}\underset{R^2}{\overset{S\text{—}C(CH_2\text{—}Y)(R^3)}{\phantom{|}}}$$

| No. | $R^1$ | $R^2$ | $R^3$ | Y | Property of the products |
|---|---|---|---|---|---|
| 9 | tetrazolyl-CH$_2$-CONH— (1-methyltetrazole) | —COOH | —CH$_3$ | —S-(1-methyl-1,2,3,4-tetrazol-5-yl) | mp 152 to 154° C |
| 10 | C$_6$H$_5$-CH$_2$CONH— | —COOH | —CH$_3$ | —S-(1-methyl-1,2,3,4-tetrazol-5-yl) | N,N'-dibenzylethylenediamine salt mp 150 to 152° (dec.) |
| 11 | C$_6$H$_5$-CH$_2$CONH— | —COOH | —CH$_3$ | —S-(benzothiazol-2-yl) | Sodium salt mp 200° C (dec.) |
| 12 | C$_6$H$_5$-CH$_2$CONH— | —COOH | —CH$_3$ | —S-(5-methyl-1,3,4-thiadiazol-2-yl) | Sodium salt mp 185 to 186° C (dec.) |

Reaction of:

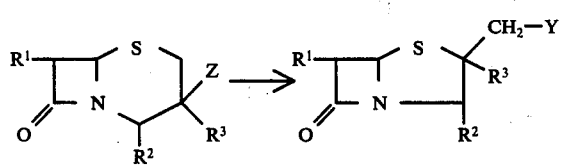

EXAMPLE 1

2,2,2-Trichloroethyl-3-bromo-3-methyl-7-(2-phenylacetamido)cepham---carboxylate (1.10 g) was dissolved in methylene chloride 15 ml) and to this solution was added aniline (0.28 g). And to the solution was added silver fluoroborate (0.45 g) under stirring under ice-cooling and the mixture was stirred for - hours at the same temperature. After the reaction was completed, the reaction mixture was filtered. The filtate was washed with a dilute aqueour solution of phosphoric acid and then with water, dried over magnesium sulfate and concentrated. The residue was subjected to column chromatography on silica gel (25 g) and eluted with chloroform. The eluate was separated into fractions of each about 20 ml and the second to eighth fractions were collected and then the solvent was distiled off to give 2,2,2-trichloroethyl 2-anilinomethyl-2-methyl-6-(2-phenylacetamido)penam-3-carboxylate (0.54 g), mp 148° to 149° C.

Infrared Absorption Spectrum (CHCl$_3$): 3400, 1780 1765, 1680 cm$^{-1}$.

| No. | $R^1$ | $R^2$ | $R^3$ | Y | Property of the product |
|---|---|---|---|---|---|
| 1 | C$_6$H$_5$-CH$_2$CONH— | —COOCH$_2$CCl$_3$ | —CH$_3$ | —N$_3$ | mp 105 to 106 °C |
| 2 | C$_6$H$_5$-CH$_2$CONH— | —COOCH$_2$CCl$_3$ | —CH$_3$ | —S-(5-methyl-1,3,4-thiadiazol-2-yl) | Oil Infrared Absorption Spectrum (CHCl$_3$) 3320, 1790, 1765, 1680 cm$^{-1}$ |
| 3 | C$_6$H$_5$-CH$_2$CONH— | —COOCH$_2$CCl$_3$ | —CH$_3$ | —S-(benzothiazol-2-yl) | Oil Infrared Absorption Spectrum (CHCl$_3$) 3400, 1790, 1765, 1680 cm$^{-1}$ |

-continued

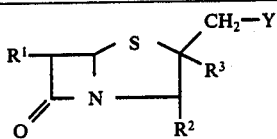

| No. | R¹ | R² | R³ | Y | Property of the product |
|---|---|---|---|---|---|
| 4 | PhCH₂CONH— | —COOCH₂CCl₃ | —CH₃ | —S-(1-methyl-1H-tetrazol-5-yl) | Oil<br>Infrared Absorption Spectrum (CHCl₃)<br>3300, 1790, 1765, 1680 cm⁻¹ |
| 5 | PhCH₂CONH— | —COOCH₂CCl₃ | —CH₃ | —S—COCH₃ | Oil<br>Infrared Absorption Spectrum (CHCl₃)<br>3390, 1790, 1765, 1690 – 1680 cm⁻¹ |
| 6 | PhCH₂CONH— | —COOCH₂CCl₃ | —CH₃ | —S—CS—N(piperidinyl) | Oil<br>Infrared Absorption Spectrum (CHCl₃)<br>3300, 1788, 1764, 1675 cm⁻¹ |
| 7 | PhCH₂CONH— | —COOCH₂CCl₃ | —CH₃ | —S-(1-methylimidazol-2-yl) | Oil<br>Infrared Absorption Spectrum (CHCl₃)<br>3200, 1790, 1770, 1678 cm⁻¹ |
| 8 | PhCH₂CONH— | —COOCH₂CCl₃ | —CH₃ | —S-(4-pyridyl) | Oil<br>Infrared Absorption Spectrum (Film)<br>3250, 1780, 1765, 1665 cm⁻¹ |
| 9 | PhOCH₂CONH— | —COOCH₃ | —CH₃ | —S-(5-methyl-1,3,4-thiadiazol-2-yl) | Infrared Absorption Spectrum (Film)<br>3300, 1785, 1745, 1690 cm⁻¹ |
| 10 | Ph-CH(NH-COOCHCH₃-cyclopropyl)-CONH— | —COOCH₂CCl₃ | —CH₃ | —S-(1-methyl-1H-tetrazol-5-yl) | Oil<br>Infrared Absorption Spectrum (Film)<br>3270, 1780, 1760, 1710, 1680 cm⁻¹ |
| 11 | Ph-CH(NH-COOCHCH₃-cyclopropyl)-CONH— | —COOCH₂CCl₃ | —CH₃ | —S-(5-methyl-1,3,4-thiadiazol-2-yl) | Oil<br>Infrared Absorption Spectrum (Film)<br>3270, 1760, 1710, 1680 cm⁻¹ |
| 12 | PhCH₂CONH— | —COOCH₂CCl₃ | —CH₃ | —OCH₃ | Oil<br>Infrared Absorption Spectrum (CHCl₃)<br>3360, 1785, 1757, 1666 cm⁻¹ |
| 13 | PhOCH₂CONH— | —COOCH₃ | —CH₃ | —NH-Ph | Oil<br>Infrared Absorption Spectrum (CHCl₃)<br>3410, 1785, 1748, 1690 cm⁻¹ |
| 14 | (1H-1,2,4-triazol-1-yl)CH₂CONH— | —COOCH₂CCl₃ | —CH₃ | —S-(1-methyl-1H-tetrazol-5-yl) | Amorphous<br>Infrared Absorption Spectrum (Nujol)<br>3220, 1780, 1760, 1700 cm⁻¹ |
| 15 | [3-(2-chlorophenyl)-5-methyl-isoxazol-4-yl]-CONH— | —COOCH₂CCl₃ | —CH₃ | —S-(1-methyl-1H-tetrazol-5-yl) | Amorphous<br>Infrared Absorption Spectrum (Nujol)<br>3300, 1780, 1770, 1665 cm⁻¹ |

-continued

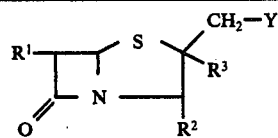

| No. | R¹ | R² | R³ | Y | Property of the product |
|---|---|---|---|---|---|
| 16 | phenyl-OCH₂CONH— | —COOCH₃ | —CH₃ | —OCH₃ | Oil<br>Infrared Absorption Spectrum (CHCl₃)<br>3370, 1787, 1742, 1685 cm⁻¹ |
| 17 | phenyl-OCH₂CONH— | —COOCH₂CCl₃ | —CH₃ | —SCN | Oil<br>Infrared Absorption Spectrum (Film)<br>1785, 1760, 1690 cm⁻¹ |
| 18 | phenyl-CH(NHCOCHCH₃-cyclopropyl)CONH— | —COOCH₂CCl₃ | —CH₃ | —SCN | Oil<br>Infrared Absorption Spectrum (Film)<br>1780, 1765, 1680 cm⁻¹ |
| 19 | (2-Cl-phenyl)-C(=N-O)-C(CH₃)=CONH— | —COOCH₂CCl₃ | —CH₃ | —SCN | Powder<br>Infrared Absorption Spectrum (Nujol)<br>1785, 1770, 1670 cm⁻¹ |
| 20 | phenyl-CH₂CONH— | —COOCH₂CCl₃ | —CH₃ | —SCN | mp 137 to 140° C |
| 21 | H₂N— | —COOCH₂CCl₃ | —CH₃ | —SCN | toluenesulfonate<br>mp 182 to 185° C (dec.) |
| 22 | phenyl-CH₂CONH— | —COOH | —CH₃ | —SCOCH₃ | N,N'-dibenzylethylenediamine salt<br>mp 105 to 107° C |
| 23 | phenyl-CH₂CONH— | —COOH | —CH₃ | —S—CS—N(piperidine) | N,N'-dibenzylethylenediamine salt<br>mp 100° C (dec.) |
| 24 | phenyl-CH₂CONH— | —COOH | —CH₃ | —NH-phenyl | mp 120° C |
| 25 | (2-Cl-phenyl)-C(=N-O)-C(CH₃)=CONH— | —COOH | —CH₃ | —S-(1-methyltetrazol-5-yl) | N,N'-dibenzylethylenediamine salt<br>mp 117 to 119° C (dec.) |
| 26 | (tetrazol-1-yl)-CH₂CONH— | —COOH | —CH₃ | —S-(1-methyltetrazol-5-yl) | mp 152 to 154° C |
| 27 | phenyl-CH₂CONH— | —COOH | —CH₃ | —S-(1-methyltetrazol-5-yl) | N,N'-dibenzylethylenediamine salt<br>mp 150 to 152° C (dec.) |
| 28 | phenyl-CH₂CONH— | —COOH | —CH₃ | —S-(benzothiazol-2-yl) | Sodium salt<br>mp 200° C (dec.) |

-continued

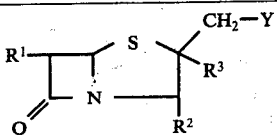

| No. | $R^1$ | $R^2$ | $R^3$ | Y | Property of the product |
|---|---|---|---|---|---|
| 29 | PhCH$_2$CONH— | —COOH | —CH$_3$ | -S-(thiadiazolyl)-CH$_3$ | Sodium salt mp 185 to 186° C (dec.) |

Reaction of:

Reaction of:

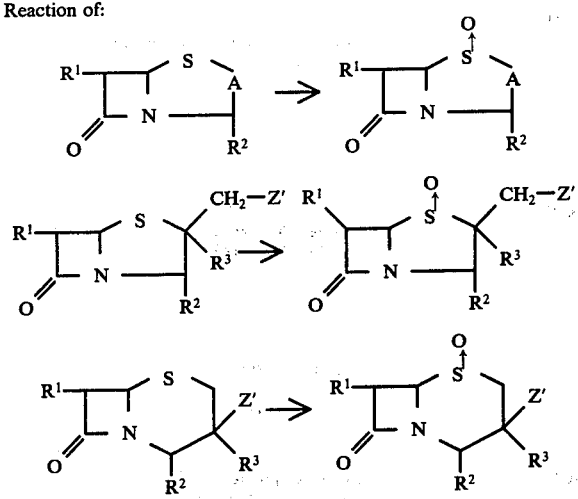

EXAMPLE 1

A solution of m-chloroperbenzoic acid (1.39 g) in chloroform (15 ml) was added to a solution of 2,2,2-trichloroethyl 2-bromomethyl-2-methyl-6-(2-phenylacetamido)penam-3-carboxylate (3.74 g) in chloroform (35 ml) under ice-cooling. The mixture was stirred under ice-cooling for 1 hour, and precipitates were filtered off. The filtrate was washed with a saturated sodium bicarbonate aqueous solution and water in turn and dried over magnesium sulfate. After the solvent was removed uner reduced pressure, the residue was crystallized by adding a little of ether. The Crystals were filtered to give colorless crystals of 2,2,2-trichloroethyl 2-bromomethyl-2-methyl-6-(2-phenylacetamido)penam-3-carboxylate-1-β-oxide (3.15 g), mp 114°-115° C (dec.).

Analysis — $C_{18}H_{18}O_5N_2$ $SCl_3$ Br: Calcd. : C38.55, H3.24, N4.99. Found : C38.40, H3.12, N 4.68.

EXAMPLE 2

2,2,2-trichloroethyl-2-bromomethyl-2-methyl-6-(2-phenylacetamido)penam-3-carboxylate (540 mg) was suspended in a mixed solution of pyridine (10 ml) and water (1 ml) at −35°-40° C. To the suspension was dropwise added isocyanuroyl chloride (110 mg). The mixture was stirred for an hour and 20 minutes and then the mixture was poured into a mixed solution of 20% aqueous phosphoric acid (50 ml) and ethyl acetate (20 ml) under ice-cooling. The ethyl acetate fraction was separated. After the water layer was extracted with ethyl acetate, the ethyl acetate extract was combined with the above-obtained ethyl acetate layer. The extract was washed with 5% phosphoric acid, water, saturated sodium bicarbonate aqueous solution and water in turn, and then dried over magnesium sulfate. After the solvent was removed, the residue was subjected to column chromatography on silica gel with chloroform. The 3rd fraction was concentrated to give 2,2,2-trichloroethyl-2-bromomethyl-2-methyl-6-(2-phenylacetamido)penam-3-carboxylate-1-β-oxide (130 mg). The 5th fraction was concentrated to give 2,2,2-trichloroethyl 2-bromomethyl-2-methyl-6-(2-phenylacetamido)-penam-3-carboxylate-1-α-oxide (170 mg).

Infrared Absorption Spectrum (CHCl$_3$) of the α-oxide compound: 3420, 1795, 1770, 1665 cm$^{-1}$.

EXAMPLE 3 m-Chloroperbenzoic acid (210 mg) was dropwise added to a solution of 2,2,2-trichloroethyl 2-thiocyanatomethyl-2-methyl-6-(2-phenylacetamido)penam-3-carboxylate (522 mg) in chloroform (10 ml) under ice-cooling. The mixture was stirred under ice-cooling for 1 hour and the solid was filtered off. The filtrate was washed with a saturated sodium bicarbonate aqueous solution and water, in turn, and then dried over magnesium sulfate. The solvent was removed to give colorless power of 2,2,2-trichloroethyl 2-thiocyanatomethyl-2-methyl-6-(2-phenylacetamido)penam-3-carboxylate-1-β-oxide (540 mg).

Infrared Absorption Spectrum (Nujol): 3330, 2130, 1797, 1778(sh.), 1677 cm$^{-1}$.

EXAMPLE 4

2,2,2-Trichloroethyl 2-thiocyanatomethyl-2-methyl-6-(2-phenylacetamido)penam-3-carboxylate (522 mg) was suspended in a mixed solution of pyridine (10 ml) and water (1 ml) at −35°-40° C. To the suspension was dropwise added isocyanuroyl chloride (110 mg) at −35°−−40° C. The mixture was stirred at −35°−−40° C for 1 hour, and then poured into a mixed solution of ice-cooled 20% phosphoric acid (50 ml) and ethyl acetate (20 ml), and then the ethyl acetate layer was separated. After the water layer was extracted with ethyl acetate, the extract was combined with the above-obtained ethyl acetate layer. The extract was washed with 5% phosphoric acid, water, saturated sodium bicarbonate aqueous solution and water, in turn, and dried over magnesium sulfate. After the solvent was distilled off, the residue was purified by column chromatography on silica gel with chloroform to give 2,2,2-trichloroethyl 2-thiocyanatomethyl-2-methyl-6-(2-phenylacetamido)penam-3-carboxylate-β-oxide (140 mg).

EXAMPLE 5

2,2,2-trichloroethyl 2-thiocyanatomethyl-2-methyl-6-(2-phenylacetamido)penam-3-carboxylate (522 mg) was suspended in a mixed solution of pyridine (12 ml) and water (12 ml) at −25°- −35° C. To the suspension was added phenyliodododichloride (550 mg). And the mixture was stirred at −25°- −35° C for 3 hours, phenyliodododichloride (550 mg) was further added to the mixture. After stirring for 1 hour, phenyliodododichloride (550 mg) was added to the mixture again. The reaction mixture was stirred for additional 1 hour, poured into a mixed solution of 20% phosphoric acid (50 ml) and ethyl acetate (20 ml), and then the ethyl acetate layer was separated. The aqueous layer was extracted with ethyl acetate, which was combined with the above-obtained ethyl acetate layer. The combined ethyl acetate layer was washed with 5% phosphoric acid, water saturated sodium bicarbonate aqueous solution and water, in turn, and then dried over magnesium sulfate. After the solvent was removed under reduced pressure, the residue was subjected to column chromatography on silica gel with a mixed solution of benzene (2 parts) and ethyl acetate (1part). The 3rd to 7th fractions were concentrated to give 2,2,2-trichloroethyl 2-thiocyanatomethyl-2-methyl-6-(2-phenylacetamido)penam-3-carboxylate-1-p-oxide (250 mg).

EXAMPLE 6

A solution of m-chloroperbenzoic acid (2.03 g) in chloroform (30 ml) was added dropwise to a solution of 2,2,2-trichloroethyl-2-chloromethyl-2-methyl-6-(2-phenylacetamido)penam-3-carboxylate (5.0 g) in chloroform (40 ml) at −10°- −5° C under stirring and then the mixture was stirred at −10°- −5° C for 1 hour. After the solid was filtered off, the filtrate was washed with a saturated sodium becarbonate aqueous solution and water, in turn, and then dried over magnesium sulfate. After removal of solvent, the residue was crystallized by adding ethanol. The crystal was filtered and recrystallized from ethanol to give 2,2,2-trichloroethyl 2chloromethyl-2-methyl-6-(2-phenylacetamido)penam-3-carboxylate-1-oxide (4.10 g), mp 130°- −131° C.

Analysis — $C_{18}H_{18}O_5N_2SCl_4$: Calcd. : C 41.87, H3.51, N 5.43, S 6.21. Found : C 41.80, H3.45, N 5.50, S 6.44.

EXAMPLE 7

Sodium tungstate (0.02 g) was added to a solution of 2-bromomethyl-2-methyl-6-(2-phenoxyacetamido)penam-3-carboxylic acid (3.1 g) in acetic acid (8 ml) at 7°-10° C under stirring and then to the mixture was added 30% aqueous hydrogen peroxide (1.2 ml). The mixture was stirred at 7°-10° C for 1 hour. After the reaction, ice-water (50 ml) was added to the reaction mixture and then extracted with ethyl acetate. The extract was washed with water and back-extracted with 5% sodium bicarbonate aqueous solution. The aqueous layer was washed with ethyl acetate twice, acidified with 5% hydrochloric acid to pH2 and then extracted with ethyl acetate. The extract was washed with water, dried and concentrated to give powder of 2-bromomethyl-2-methyl-6-(2-phenoxyacetamido)penam-3-carboxylic acid-1-oxide (2 g).

Infrared Absorption Spectrum (CHCl$_3$). 3350, 1795, 1740, 1688 cm$^{-1}$.

EXAMPLE 8

A solution of m-chloroperbenzoic acid (0.445 g) in chloroform (5ml) was added to a solution of 2,2,2-trichloroethyl 3-bromo-3-methyl-7-(2-phenylacetamido)cepham-4-carboxylate (1.21 g) under stirring at −5° to −10° C, and the mixture was stirred for an hour at the same temperature. After the reaction, the reaction mixture was washed with 5% sodium bicarbonate aqueous solution and with water in turn and then dried. After the solvent was distilled off, the residue was crystallized by adding ether. Thus obtained crystals were recrystallized from ethanol to give 2,2,2-trichloroethyl 3-bromo-3-methyl-7-(2-phenylacetamido)cepham-4-carboxylate-1-oxide (1.10 g), mp 159° to 161° C.

Reaction of:

Reaction of:

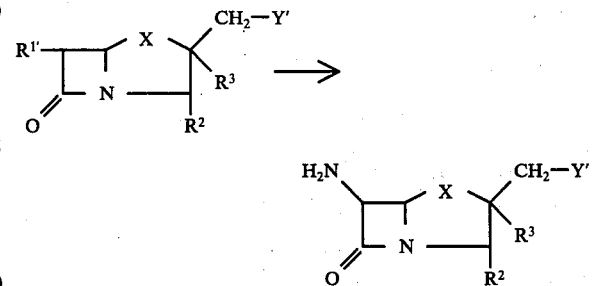

EXAMPLE 1

2,2,2-Trichloroethyl 2-bromomethyl-2-methyl-6-(2-phenylacetamido)-penam-3-carboxylate-1-oxide (1.12 g) was dissolved in dried methylene chloride (10 ml). To this solution were added dimethyl aniline (0.36 g) under cooling at −15° C and then phosphorus pentachloride (0.6 g), and the mixture was stirred for 3 hours. To the solution was added anhydrous methanol (0.7 g) under cooling at −40° C and the solution was stirred for 2 hours and further stirred for 1 hour at −15° C. After the reaction, precipitated crystals were collected by filtration, washed with a small amount of methylene chloride and then dried to give 2,2,2-trichloroethyl 2-bromomethyl-2-methyl-6-aminopenam-3-carboxylate-1-oxide hydrochloride (0.70 g), mp 147° to 154° C (dec.).

Infrared Absorption Spectrum (Nujol): 1820, 1800, 1760 cm$^{-1}$.

EXAMPLE 2

2,2,2-Trichloroethyl 2-bromomethyl-2-methyl-6-(2-phenylacetamido)penam-3-carboxylate (10.8 g) was dissolved in dried methylene chloride (300 ml). To this solution were added under cooling at −35° C dried dimethylaniline (3.6 g) and then phosphorus pentachloride (6.4 g) and the mixture was stirred for 2.5 hours at the same temperature. To the solution was added dropwise anhydrous methanol (6.4 g) at the same temperature and the mixture was stirred for 1 hour at −15° C. Water (6.3 ml) was added to the solution and the solution was vigorously stirred for 30 minutes. After the reaction, precipitates were collected by filtration, washed with methylene chloride and further with ether and then dried to give powdery 2,2,2-trichloroethyl 2-bromomethyl-2-methyl-6-aminopenam-3-carboxylate hydrochloride (7.8 g).

Infrared Absorption Spectrum (Nujol): 3330 - 3400, 1790, 1770 cm$^{-1}$.

EXAMPLE 3

2,2,2-Trichloroethyl 2-thiocyanatomethyl-2-methyl-6-(2-phenylacetamido)-penam-3-carboxylate (0.53 g) was dissolved in dried methylene chloride (10 ml). To this solution were added under cooling at $-20°$ to $-30°$ C dimethylaniline (0.43 g) and then phosphorus pentachloride (0.23 g) and the mixture was stirred for 1.5 hours. Further, to the solution was added dropwise anhydrous methanol (0.3- g) and the solution was stirred for 5 hours. Water (7 ml) was added to the solution at 0° C and the mixture was stirred for 10 minutes. Aqueous layer was separated from the mixture. The aqueous layer was adjusted to pH9 by adding 1N-sodium hydroxide aqueous solution and extracted with ethyl acetate (10 ml). The extract was dried over magnesium sulfate and the solvent was distilled off. The residue was dissolved in a small amount of ethyl acetate and to the solution were added toluene-sulfonic acid monohydrate (0.1 g) and ethyl acetate (5 ml). The mixture was cooled and precipitated crystals were collected by filtration to give 2,2,2-trichloroethyl 2-thiocyanatomethyl-2-methyl-6-aminopenam-3-carboxylate toluenesulfonate (0.06 g), mp 182° to 185° C (dec.).

Infrared Absorption Spectrum (Nujol): 2150, 1795, 1750 cm$^{-1}$.

Reaction of:

Reaction of:

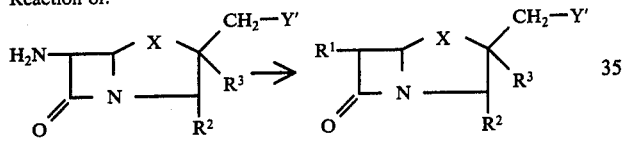

EXAMPLE 1

To a sodium of ethyl chlorocarbonate (1.95 g) in dried methylene chloride (120 ml) was added dropwise under cooling $-5°$ C a solution of N-(1-cyclopropylethoxy)-carbonylphenylglycine (4.74 g) and triethylamine (1.83 g) in dried methylene chloride (50 ml). The solution containing a mixed anhyride of N-(1-cyclopropylethoxy)carbonylphenylglycine and ethyl chlorocarbonte prepared by stirring the above mixture for 1 hour at eht same temperature was cooled at $-30°$ to $-35°$ C. To this solution were added dropwise a solution of 2,2,2-trichloroethyl 2-bromomethyl-2-methyl-6-aminopenam-3-carboxylate hydrochloride (6.95 g) and triethylamine (3.0 g) in dried methylene chloride (100 ml), and the mixture was stirred for 3 hours. After the reaction was completed, the reaction mixture was washed with 5% hydrochloric acid, water, 5% sodium bicarbonate aqueous solution andwater in turn and then dried. The solvent was distilled off to give amorphous, 2,2,2-trichloroethyl 2-bromoethyl-2-methyl-6-[N-(1-cyclopropylethoxy)-phenylglycyl]aminopenam-3-carboxylate (9.7 g).

Infrared Absorption Spectrum (CHCl$_3$): 3410, 1785, 1765, 1690 cm$^{-1}$.

EXAMPLE 2

To a solution of pivaloyl chloride (1.4 g) in dried methylene chloride (100 ml) was added dropwise under cooling at $-5°$ C a solution of 1H-tetrazol-1-acetic acid (1.81 g) and triethylamine (1.4 g) in dried methylene chloride (30 ml), and the mixture was stirred for 2 hours at the same temperature. The solution containing a mixed anhydride of 1H-tetrazole-1-acetic acid and pivalic acid prepared above was cooled at $-35°$ C and to the solution were added dropwise a solution of 2,2,2-trichloroethyl 2-bromoethyl-2-methyl-6-aminopenam-3-carboxylate hydrochloride (4.0 g) and triethlamine (2.0 g) in dried methylene chloride (80 ml), after which the mixture was stirred for 4 hours at the same temperature. After the reaction was completed, the reaction mixture was post-treated in the similar manner as described in Example 1 to give oily 2,2,2-tricloroethyl 2-bromoethyl-2-methyl-6-[2-(1H-tetrazol-1-yl)acetamido]penam-3-carbodylate (3.85 g).

Infrared Absorption Spectrum (Film): 3250, 1783, 1765, 1635 cm$^{-1}$.

EXAMPLE 3

A solution of 2,2,2-trichloroethyl 2-bromoethyl-2-methyl-6-aminopenam-3-carboxylate hydrochloride (6.95 g) and triethylamine (3.0 g) in dried methylene chloride (100 ml) was cooled at $-25°$ C. To this solution was added dropwise a solution of 3-(2-chlorophenyl)-5-methylisoxazole-4-carbonyl chloride (4.5 g) in dried methylene chloride (30 ml), and the mixture was stirred for 33 hours at the same temperature. After the reaction was completed, the reaction mixture was post-treated in the similar manner as described in Example 1 to give oily 2,2,2-trichloroethyl 2-bromoethyl-2-methyl-6-[3-(2-chlorophenyl)-5-methylisoxazole-4-carboxamido]penam-3-carboxylate (6.75 g).

Infrared Absorption Spectrum (Film): 3370, 1790, 1765, 1670 cm$^{-1}$.

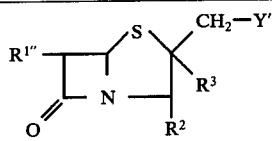

| No. | R$^{1'''}$ | R$^2$ | R$^3$ | Y' | X | Property of the product |
|---|---|---|---|---|---|---|
| 1 | ⟨phenyl⟩-CH$_2$CONH— | —COOCH$_2$CCl$_3$ | —CH$_3$ | —N$_3$ | —S— | mp. 105 to 106° C |
| 2 | ⟨phenyl⟩-CH$_2$CONH— | —COOCH$_2$CCl$_3$ | —CH$_3$ | -S-⟨N-N/S⟩-CH$_3$ | —S— | Oil Infrared Absorption Spectrum(CHCl$_3$) 3320, 1790, 1765, 1680 cm$^{-1}$ |

-continued

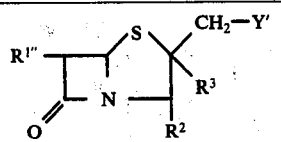

| No. | R[1"] | R[2] | R[3] | Y' | X | Property of the product |
|---|---|---|---|---|---|---|
| 3 | phenyl-CH₂CONH— | —COOCH₂CCl₃ | —CH₃ | —S—(benzothiazol-2-yl) | —S— | Oil<br>Infrared Absorption Spectrum(CHCl₃) 3400, 1790, 1765, 1680 cm⁻¹ |
| 4 | phenyl-CH₂CONH— | —COOCH₂CCl₃ | —CH₃ | —S—(1-methyltetrazol-5-yl) | —S— | Oil<br>Infrared Absorption Spectrum(CHCl₃) 3300, 1790, 1765, 1680 cm⁻¹ |
| 5 | phenyl-CH₂CONH— | —COOCH₂CCl₃ | —CH₃ | —S—COCH₃ | —S— | Oil<br>Infrared Absorption Spectrum(CHCl₃) 3390, 1790, 1765, 1690 to 1680 cm⁻¹ |
| 6 | phenyl-CH₂CONH | —COOCH₂CCl₃ | —CH₃ | —S—CS—N(piperidinyl) | —N— | Oil<br>Infrared Absorption Spectrum(CHCl₃) 3300, 1788, 1764, 1675 cm⁻¹ |
| 7 | phenyl-CH₂CONH— | —COOCH₂CCl₃ | —CH₃ | —S—(1-methylimidazol-2-yl) | —S— | Oil<br>Infrared Absorption Spectrum(CHCl₃) 3200, 1790, 1770, 1678 cm⁻¹ |
| 8 | phenyl-CH₂CONH— | —COOCH₂CCl₃ | —CH₃ | —S—(pyridin-4-yl) | —S— | Oil<br>Infrared Absorption Spectrum(Film) 3250, 1780, 1765, 1665 cm⁻¹ |
| 9 | phenyl-OCH₂CONH— | —COOCH₃ | —CH₃ | —S—(5-methyl-1,3,4-thiadiazol-2-yl) | —S— | Oil<br>Infrared Absorption Spectrum(Film) 3300, 1785, 1745, 1690 cm⁻¹ |
| 10 | phenyl-CHCONH—, NH—COOCHCH₃, CH(CH₂—CH₂) | —COOCH₂CCl₃ | —CH₃ | —S—(1-methyltetrazol-5-yl) | —S— | Oil<br>Infrared Absorption Spectrum(Film) 3270, 1780, 1760, 1710, 1680 cm⁻¹ |
| 11 | phenyl-CHCONH—, NH—COOCHCH₃, CH(CH₂—CH₂) | —COOCH₂CCl₃ | —CH₃ | —S—(5-methyl-1,3,4-thiadiazol-2-yl) | —S— | Oil<br>Infrared Absorption Spectrum(Film) 3270, 1760, 1710, 1680 cm⁻¹ |
| 12 | phenyl-CH₂CONH— | —COOCH₂CCl₃ | —CH₃ | —OCH₃ | —S— | Oil<br>Infrared Absorption Spectrum(CHCl₃) 3360, 1785, 1757, 1666 cm⁻¹ |
| 13 | phenyl-OCH₂CONH— | —COOCH₃ | —CH₃ | —NH-phenyl | —S— | Oil<br>Infrared Absorption Spectrum(CHCl₃) 3410, 1785, 1748, 1690 cm⁻¹ |
| 14 | (tetrazolyl)CH₂CONH— | —COOCH₂CCl₃ | —CH₃ | —S—(1-methyltetrazol-5-yl) | —S— | Amorphous |
| 15 | (3-chloro-5-methylisoxazol-4-yl)CONH— | —COOCH₂CCl₃ | —CH₃ | —S—(1-methyltetrazol-5-yl) | —S— | Amorphous<br>Infrared Absorption Spectrum(Nujol) 3300, 1780, 1770, 1665 cm⁻¹ |
| 16 | phenyl-OCH₂CONH— | —COOCH₃ | —CH₃ | —OCH₃ | —S— | Oil<br>Infrared Absorption Spectrum(CHCl₃) 3370, 1787, 1742, 1685 cm⁻¹ |

-continued

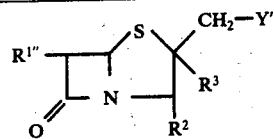

| No. | R¹″ | R² | R³ | Y′ | X | Property of the product |
|---|---|---|---|---|---|---|
| 17 | Ph-CH₂CONH— | —COOCH₂CCl₃ | —CH₃ | —N(pyridinyl) | —S— | mp 148 to 149° C |
| 18 | Ph-OCH₂CONH— | —COOCH₂CCl₃ | —CH₃ | —SCN | —S— | Oil Infrared Absorption Spectrum(Film) 1785, 1760, 1690 cm⁻¹ |
| 19 | Ph-CHCONH— with NHCOCHCH₃ / CH / CH₂—CH₂ | —COOCH₂CCl₃ | —CH₃ | —SCN | —S— | Oil Infrared Absorption Spectrum(Film) 1780, 1765, 1680 cm⁻¹ |
| 20 | (2-Cl-phenyl)-C(=N-O-)—C(CH₃)=...CONH— | —COOCH₂CCl₃ | —CH₃ | —SCN | —S— | Powder Infrared Absorption Spectrum(Nujol) 1785, 1770, 1670 cm⁻¹ |
| 21 | Ph-CH₂CONH— | —COOCH₂CCl₃ | —CH₃ | —SCN | —S— | mp 137 to 140° C |
| 22 | Ph-CH₂CONH— | —COOH | —CH₃ | —SCOCH₃ | —S— | N,N'-dibenzylethyl-enediamine salt mp 105 to 107° C |
| 23 | Ph-CH₂CONH— | —COOH | —CH₃ | —S—CS—N(piperidinyl) | —S— | N,N'-dibenzylethyl-enediamine salt mp 100° C (dec.) |
| 24 | Ph-CH₂CONH— | —COOH | —CH₃ | —NH-Ph | —S— | mp 120° C |
| 25 | (2-Cl-phenyl)-C(=N-O-)—C(CH₃)=...CONH— | —COOH | —CH₃ | —S-(1-methyl-tetrazol-5-yl) | —S— | N,N'-dibenzylethyl-enediamine salt mp 117 to 119° C (dec.) |
| 26 | (tetrazolyl)CH₂CONH— | —COOH | —CH₃ | —S-(1-methyl-tetrazol-5-yl) | —S— | mp 152 to 154° C |
| 27 | Ph-CH₂CONH— | —COOH | —CH₃ | —S-(1-methyl-tetrazol-5-yl) | —S— | N,N'-dibenzylethyl-enediamine salt mp 150 to 152° C (dec.) |
| 28 | Ph-CH₂CONH— | —COOH | —CH₃ | —S-(benzothiazol-2-yl) | —S— | Sodium salt mp 200° C (dec.) |
| 29 | Ph-CH₂CONH— | —COOH | —CH₃ | —S-(5-methyl-1,3,4-thiadiazol-2-yl) | —S— | Sodium salt mp 185 to 186° C (dec.) |
| 30 | Ph-CH₂CONH— | —COOCH₂CCl₃ | —CH₃ | —SCN | O↑—S—↓O | Colourless powder |
| 31 | Ph-CH₂CONH— | —COOCH₂CCl₃ | —CH₃ | —Br | O↑—S— | mp 114 to 115° C (dec.) |
| 32 | Ph-CH₂CONH— | —COOCH₂CCl₃ | —CH₃ | —Br | O↑—S— α-oxide | Amorphous |

-continued

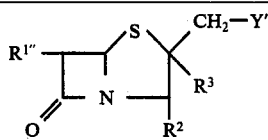

| No. | R1''' | R2 | R3 | Y' | X | Property of the product |
|---|---|---|---|---|---|---|
| 33 | ⌬-CH₂CONH— | —COOCH₂CCl₃ | —CH₃ | —Br | —S— | mp 90 to 93° C |
| 34 | ⌬-CH₂CONH— | —COOCH₂CCl₃ | —CH₃ | —Cl | —S— | mp 104 to 105° C |
| 35 | ⌬-OCH₂CONH— | —COOH | —CH₃ | —Br | —S— | mp 164.5 to 165.5° C |
| 36 | ⌬-CHCONH— \| NHCOOCH₂CCl₃ | —COOCH₂CCl₃ | —CH₃ | —Br | —S— | Powder |
| 37 | ⌬-OCH₂CONH— | —COOCH₃ | —CH₃ | —Br | —S— | Oil<br>Infrared Absorption Spectrum 3350, 1785, 1748, 1690 cm⁻¹ |
| 38 | ⌬-CH₂—CONH— | —COOCH—CH₃ \| CH \| CH₂—CH₂ | —CH₃ | —Br | —S— | Oil |
| 39 | N—N—CH₂CONH— O⟨±\|  ⟩C—CH O | —COOCH₂CCl₃ | —CH₃ | —Br | —S— | Amorphous |
| 40 | ⌬-CH₂CONH | —COOCH₂-⌬(C(CH₃)₃)(OH)(C(CH₃)₃) | —CH₃ | —Br | —S— | White crystalline powder |
| 41 | HO-⌬-CHCONH— \| NHCOOCHCH₃ \| CH \| CH₂—CH₂ | —COOCH₂CCl₃ | —CH₃ | —Br | —S— | Powder |
| 42 | CH₃SCH₂CONH— | —COOCH₂CCl₃ | —CH₃ | —Br | —S— | mp 71 to 73° C (dec.) |
| 43 | ⟨N-S-N⟩-CH₂CONH— | —COOCH₂CCl₃ | —CH₃ | —Br | O↑<br>—S— | mp 115 to 116° C (dec.) |
| 44 | ⌬-CH₂CONH— | —COOCH₂CCl₃ | —CH₃ | Cl | O↑<br>—S— | mp 130 to 131° C |

Reaction of:

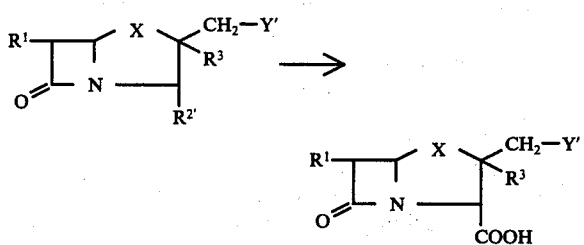

EXAMPLE 1

Acetic acid (1 ml) and zinc powder (0.75 g) were added to a solution of 2,2,2-trichloroethyl 2-acetylthiomethyl-2-methyl-6-(2-phenylacetamido) penam-3-carboxylate (0.65 g) in dimethylformamide (3 ml) under ice-cooling and the mixture was stirred for 2 hours at the same temperature. After the reaction, the reaction mixture was filtered and the filtrate was poured into 5% hydrochloric acid (20 ml) and then extracted with ethy acetate. The extract was washed with water, dried and the solvent was distilled off to give oil (0.365 g). After dissolving the oil in acetone (0.7 ml), to this solution was added a solution of N,N'-dibenzylethylenediamine diacetate (0.142 g) in water (5 ml) and precipitated powder was filtered. The powder has purified by reprecipitation method from a mixture of methanol and water to give N,N'-dibenzyl-ethylenediamine 2-acetylthiomethyl-2-methyl-6-(2-phenylacetamido)penam-3-carboxylate (0.211 g) mp. 105° t 107° C.

Analysis for $C_{18}H_{19}N_2O_5S_2.\frac{1}{2} C_{16}H_{22}N_2.H_2O$: Calc'd C 57.19, H 5.87, N 7.69. Found: C 57.18, H 5.58, N 7.44.

Infrared Absorption Spectrum (Nujol): 3300, 1772, 1690, 1670 cm$^{-1}$.

EXAMPLE 2

Acetic acid (1 ml) and zinc powder (0.80 g) were added to a solution of 2,2,2-trichloroethyl-2-piperidine-thiocarbonylthiomethyl-2-methyl-6-(2-phenylacetamido)penam-3-carboxylate (0.95 g) in dimethylformamide (5 ml) under ice-cooling and the mixture was stirred for 1 hour and 40 minutes. After the reaction, zinc powder was filtered off and the filtrate was poured into ethyl acetate. The solution was washed with 3% hydrochloric acid and then with water (four times) and dried over magnesium sulfate. After dryng, the solvent was distilled off and the residue was dissolved in a small amount of methanol. To this solution was added on aqueous solution of N,N'-dibenzylethylenediamine diacetate and precipitates were collected by filtration, washed with water to give N,N'-dibenzylethylenediamine2-piperidinothiocarbonylthiomethyl-2-methyl-6-(2-phenylacetamido)penam-3-carboxylate (0.30 g), mp. 100° C (dec.).

Analysis for $C_{22}H_{26}O_4N_3S_3.\frac{1}{2} C_{16}H_{22}N$: Calc'd: C 57.03, H 6.22, N 8.87. Found: C 57.00, H, 5.87, N, 8.60.

Infrared Absorption Spectrum (Nujol): 3280, 1777, 1660 cm$^{-1}$.

EXAMPLE 3

2,2,2-Trichloroethyl 2-anilinomethyl-2-methyl-6-(2-phenylacetamido) penam-3-carboxylate (1.00 g) was dissolved in dimethylformamide (5 ml). To this solution were added acetic acid (0.5 ml) and then zinc powder under cooling at −15° C and the mixture was stirred for 6 hours. After the reaction, zinc powder was filtered off and the filtrate was poured into ethyl acetate. The solution was washed 4 times with water and dried pver magnesium sulfate. After drying, the solvent was distilled off and and the residue was dissolved in a small amount of methanol and then pulverized by adding water to the solution. The powder was collected by filtration, washed with water and dried to give 2-anilinomethyl-2-methyl-6-(2-phenylacetamido)-penam-3-carboxylic acid (0.50 g), mp. 120° C.

Analysis for $C_{22}H_{23}O_4N_3S.\frac{1}{2} H_2O$: Calc'd: C 60.81, H 5.56, N 9.67. Found: C 60.49, H 5.40, N 9.44.

Infrared Absorption Spectrum (Nujol): 3400, 1780, 1745 cm$^{-1}$.

EXAMPLE 4

2,2,2-Trichloroethyl 2-(1-methyl-1H-tetrazol-5-yl)thiomethyl-2-methyl-6-[3-(2-chlorophenyl)-5-methylisoxazole-4-carboxamido]penam-3-carboxylate (0.67 g) was dissolved in dimethylformamide (5 ml). To this solution were added acetic acid (0.8 ml) and zinc powder (0.7 g) under cooling at −15° C and the mixture was stirred for 2 hours at the same temperature. After the reaction, zinc powder was filtered off and the filtrate was poured into 5% hydrochloric acid (20 ml) and then extracted with ethyl acetate. The extract was washed with water, dried and the solvent was distilled off. The residue was dissolved in methanol (0.8 ml) and to this solution was added a solution of N,N'-dibenzylethylenediamine diacetate (0.18 g) in water (5 ml) and precipitates were collected by filtration, washed with water and dried to give N,N'-dibenzylethylenediamine 2-(1-methyl-1H-tetrazol-5-yl)thiomethyl-2-methyl-6-[3-(2-chlorophenyl)-5-methylisoxazole-4-carboxamido]penam-3-carboxylate (0.24 g), mp. 117° to 119° C (dec.).

Infrared Absorption Spectrum (Nujol): 3400, 1778, 1665 cm$^{-1}$.

EXAMPLE 5

2,2,2-Trichloroethyl 2-(1methyl-1H-tetrazol-5-yl)thiomethyl-2-methyl-6-[2-(1H-tetrazol-1-yl) acetamido]penam-3-carboxylate (0.6 g) was dissolved in dimethylformamide (5 ml). To this solution were added acetic acid (0.9 ml) and zinc powder (0.8 g) under cooling at −15° C and the mixture was stirred for 1.5 hours at the same temperature. After the reaction, zinc powder was filtered off and the filtrate was poured into 5% hydrochloric acid (20 ml) and then extracted with ethyl acetate. The extract was washed with water, dried and the solvent was distilled off. The residue was crystallized from ether to give 2-(1-methyl-1H-tetrazol-5-thiomethyl-2-methyl-6-[2-(1H-tetrazol-1-yl) acetamido]penam-3-carboxylic acid (0.25 g), mp. 152° l to 154° C.

Infrared Absorption Spectrum (Nujol): 3230, 1780, 1738, 1692 cm$^{-1}$.

EXAMPLE 6

2,2,2-Trichloroethyl 2-(1-methyl-1H-tetrazol-5-yl)thiomethyl-2-methyl-6-(2-phenylacetamido)penam-3-carboxylate (0.94 g) was dissolved in dimethylformamide (5 ml). To this solution were added under ice-cooling acetic acid (0.7 ml) and then zinc powder (0.80 g) under stirring and the mixture was stirred for 2.5 hours. After the reaction, zinc powder was filtered off and the filtrate was dissolved in ethyl acetate. The solution was washed with 3% hydrochloric acid, 3 times with water and dried over magnesium sulfate. After drying, the solvent was distilled off and the residue was dissolved in a small amount of methanol and then crystallized by adding an aqueous solution of N,N'-dibenzylethylenediamine diacetate (0.36 g). Crystals were collected by filtration and washed with a mixture of ethanol and water and dried to give N,N'-dibenzylethylenediamine 2-(1-methyl-1H-tetrazol-5-yl) thiomethyl-2-methyl-6-(2-phenylacetamido)penam-3-carboxylate (0.50 g), mp. 150° to 152° C (dec.).

Analysis for $C_{18}H_{18}O_4N_6S_2.\frac{1}{2} O_{16}H_{22}N_2.\frac{1}{2} H_2O$: Calc'd: C 54.48, H 5.28, N 17.17. Found: C 54.45, H 5.29, N 17.00.

Infrared Absorption Spectrum (Nujol): 3370, 1763, 1674 cm$^{-1}$.

EXAMPLE 7

2,2,2-Trichloroethyl 2-chloromethyl-2-methyl-6-(2-phenylacetamido) penam-3-carboxylate (1.5 g) was dissolved in dried dimethylformamide (8 ml) and to this solution were added formic acid (1.5 ml) and then zinc powder (1.5 g) under stirring while ice-cooling. After stirring for 2 hours at the same temperature, zinc powder was filtered off and washed with dimethylformamide (5 ml). The filtrate and the washings were added to a mixed cool solution of ethylacetate (30 ml) and 5% hydrochloric acid (15 ml). After extracting with ethyl acetate, the extract was washed with water and dried over magnesium sulfate. The gummy substance (1.16 g) obtained by distilling off the solvent inder reduced pressure was crystallized from a mixed solvent of ethyl acetate and isopropyl ether to give 2-chloromethyl-2-methyl-6-(2-phenylacetamido) penam-3-carboxylic acid (660 mg) mp. 110° to 112° C (dec.).

Analysis for $C_{16}H_{17}N_2O_4SCl$: Calc'd: 52.10, H 4.65, N 7.60, S 8.69, Cl 9.61. Found: C 51.90, N 4.73, N 7.46, S 8.67, Cl 9.34.

Infrared Absorption Spectrum (Nujol): 3325, 1788, 1730, 1635 cm⁻¹.

EXAMPLE 8

2,2,2-Trichloroethyl 2-(benzothiazol-2-yl)thiomethyl-2-methyl-6-(2-phenylacetamido)penam-3-carboxylate (0.90 g) was dissolved in dimethylformamide (5 ml). To this solution were added acetic acid (0.7 ml) under ice-cooling and then zinc powder (0.80 g) under stirring, and then the mixture was stirred for 2 hours. After zinc powder was filtered off, the filtrate was dissolved in ethyl acetate and the solution was wshed with 3% hydrochloric acid and then 3 times with water and thereafter dried over magnesium sulfate. The residue obtained by distilling off the solvent was dissolved in a small amount of acetone. To this solution was added a solution of sodium 2-ethylhexanoate (250 mg) in acetone (5 ml) and the solution was again concentrated. The residue was crystallized by adding ethanol and the crystals were collected by filtration, washed with a small amount of ethanol and dried to give sodium 2-(benzothizol-2-yl)thiomethyl-2-methyl-6-(2-phenylacetamido)penam-3-carboxylate (0.50 g), mp. 200° C (dec.).

Infrared Absorption Spectrum (Nujol): 3400, 1760, 1670, 1600 cm⁻¹.

EXAMPLE 9

2,2,2-trichloroethyl 2-(5-metyl-1,3,4-thiadiazol-2-yl)thiomethyl-2-methyl-6-(2-phenylacetamido)-penam-3-carboxylate (0.80 g) was dissolved in dimethylformamide (5 ml). To this solution were added acetic acid (0.5 ml) and then zinc powder (0.80 g) under ice-cooling and the mixture was stirred for 2 hours. Zinc powder was filtered off and the filtrate was dissolved in ethyl acetate. The solution was washed with 5% hydrochloric acid and then 4 times with water and thereafter dried over magnesium sulfate. The residue obtained by distilling off the solvent was dissolved in a small amount of ethyl acetate and to the solution was added a solution of sodium 2-ethylhexanoate (250 mg) in acetone (5 ml), and then the solution was concentrated. The residue was pulverized from ethyl acetate and further the powder was crystallized from ethanol. The crystals were collected by filtration, washed with ethanol and dried to give sodium 2-(5-methyl-1,3,4-thiadiazol-2-yl)thiomethyl-2-methyl-6-(2-phenylacetamido)penam-3-carboxylate (0.28 g), mp. 185° to 186° C (dec.).

Infrared Absorption Spectrum (Nujol): 3200, 1757, 1670, 1625 cm⁻¹.

In the similar manner, the following compound was obtained. (1) 2-Bromomethyl-2-methyl-6-(2-phenoxyacetamido)penam-3-carboxylic acid (mp. 164.5° to 165.5° C).

Reaction of:

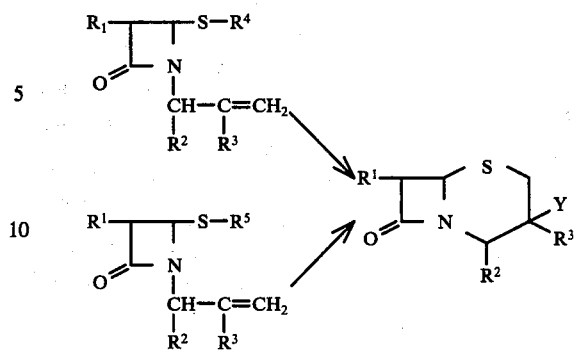

EXAMPLE 1

Methyl 2-oxo-3-(2-phenoxyacetamido)-4-(benzothiazol-2-yl)-dithio-α-isopropenyl-1-azetidineacetate (454 mg) was dissolved in methylene chloride (20 ml). To this solution was added methanol (5 ml) and thereafter added boron trifluoride etherate (0.124 g) at 0° C. The mixture was stirred for 3 hours at the same temperature and further stirred for 2 hours at 5° to 10° C. After the reaction, the mixture was washed with 5% sodium bicarbonate aqueous solution and with water. After drying the mixture, the mixture was concentrated ane the oily residue (250 mg) was purified by column chromatography on silica gel to give oily methyl 3-methyl-3-methoxy-7-(2-phenoxyacetamido)-cepham-4-carboxylate.

Infrared Absorption Spectrum (CHCl₃): 3400,1772, 1739, 1688 cm⁻¹.

EXAMPLE 2

Methyl 2-oxo-3-(2-phenoxyacetamido)-4-(benzothiazol-2-yl)dithio-α-isopropenyl-1-azetidineacetate (1.06 g) was dissolved in methylene chloride (20 ml). To this solution were added aniline (0.28 g) and then silver fluoroborate (0.80 g) and thereafter the mixture was stirred for 2 days at room temperature. After the reaction, the reaction mixture was filtered and the filtrate was washed with a dilute phosphoric acid aqueous solution and then with water. After drying the mixture, the mixture was concentrated and the residue was purified by column chromatography on silica gel (25 g) to give methyl 3-metyl-3-anilino-7-(2-phenoxyacetamido)cepham-4-carboxylate )0.38 g), mp. 129° to 130° C.

EXAMPLE 3

2,2,2-Trichloroethyl 2-oxo-3-(2-phenylacetamido)-4-(benzothiazol-2-yl)dithio-α-isopropenyl-1-azetidineacetate (1.26 g) was dissolved in ethyl acetate (15 ml). To this solution was added acetic acid (5 ml) and then silver acetate (0.68 g) under stirring at room temperature. The mixture was stirred for 4 hours at the same temperature. After the reaction, the reaction mixture was filtered and the filtrate was washed with water and then with 5% sodium bicarbonate aqueous solution. The solution was filtered again and the filtrate was washed with water and then dried. The solvent was distilled off and the residue was purified by thin layer chromatography using a mixture of acetone: benzene (1:9) to give amorphous 2,2,2-trichloroethyl 3-acetoxy-3-methyl-7-(2-phenylacetamido)cepham-4-carboxylate.

Infrared Absorption Spectrum (CHCl₃): 3425, 1780, 1750, 1680 cm⁻¹.

EXAMPLE 4

Methyl 2-oxo-3-(2-phenoxyacetamido)-4-(benzothiazol-2-yl)dithio-α-isopropenyl-1-azetidineacetate (2.12 g) was dissolved in methanol (80 ml). To this solution was added silver nitrate (0.68 g) and the mixture was refluxed for 28 hours. After the reaction, precipitates were filtered and the filtrate was concentrated. The obtained residue was extracted with ethyl acetate and the extract was washed with water and then dried. The solvent was distilled off and the obtained residue was purified by column chromatography on silica gel using chloroform as developing solvent to give pale yellow oil of methyl 3-methoxy-3-methyl-7-(2-phenoxyacetamido)cepham-4-carboxylate (620 mg.).

Infrared Absorption Spectrum (CHCl$_3$): 3400, 1772, 1739, 1688 cm$^{-1}$.

Similar result was obtained using methylene chloride as solvent and silver fluoroborate instead of silver nitrate.

EXAMPLE 5

Methyl 2-oxo-3-(2-phenoxyacetamido)-4-(benzothiazol-2-yl)dithio-α-isopropenyl-1-azetidineacetate (0.53 g) was idssolved in methanol (20 ml). To this solution was added silver acetate (0.17 g) and the mixture was refluxed for 39 hours. After the reaction, the reaction mixture was post-treated in the similar manner as described in Example 1 to give oily methyl 3-methyl-3-methoxy-7-(2-phenoxyacetamido)-cepham-4-carboxylate (200 mg).

EXAMPLE 6

A mixture of methyl 2-oxo-3-(2-phenoxyacetamido)-4-(benzothiazol-2-yl)-dithio-α-isopropenyl-1-azetidineacetate (0.53 g), mercuric acetate (0.3 g) and methanol (20 ml) were refluxed for 48 hours. After the reaction, the reaction mixture was post-treated in the similar manner as described in Example 1 to give oily methyl 3-methyl-3-methoxy-7-(2-phenoxyacetamido)cepham-4-carboxylate (180 mg).

EXAMPLE 7

Methyl 2-oxo-3-(2-phenoxyacetamido)-4-(benzothiazol-2-yl)dithio-α-isopropenyl-1-azetidineacetate (0.53 g) was dissolved in methanol (20 ml). To this solution was added mercuric chloride (0.27 g) and the mixture was refluxed for 24 hours. After the reaction, the reaction mixture was post-treated in the similar manner as described in Example 1 to give oily methyl 3-methyl-3-methoxy-7-(2-phenoxyacetamido)cepham-4-carboxylate (220 mg).

EXAMPLE 8

Methyl 2-oxo-3-(2-phenoxyacetamido)-4-benzothiazol-2-yl)-dithio-α-isopropenyl-1-azetidineacetate (0.53 g) was dissolved in methanol (20 ml). To this solution was added cupric oxide (0.15 g), and the mixture was refluxed for 72 hours. After the reaction, the reaction mixture was post-treated in the similar manner as described in Example 1 to give oily methyl 3-methyl-3-methoxy-7-(2-phenoxyacetamido)cepham-4-carboxylate (50 mg).

EXAMPLE 9

2,2,2-Trichloroethyl 2-oxo-3-(2-phenylacetamido)-4-(benzothiazol-2-yl)dithio-α-isopropenyl-1-azetidineacetate (0.63 g) and p-toluenesulfonic acid monohydrate (0.19 g) were dissolved in a mixture of methanol (15 ml) and methylene chloride (5 ml). The mixture was stirred for 4.5 hours at 50° C. After the reaction, methanol and methylene chloride were distilled off and the residue was dissolved in ethyl acetate (10 ml). The ethyl acetate layer was washed with a saturated sodium bicarbonate aqueous solution and then with water and thereafter dried over magnesium sulfate. The residue obtained by removing the solvent was purified by column chromatography on silica gel using chloroform as developing solvent to give 2,2,2-trichloroethyl 3-methyl-3-methoxy-7-(2-phenylacetamido)-cepham-4-carboxylate (120 mg), mp. 132° to 133° C.

The following compounds were obtained by using the same procedures as those of the Examples 1 to 9.
1. 2,2,2-Trichloroethyl 3-methyl-3-azido-7-(2-phenylacetamido)cepham-4-carboxylate (mp. 136° to 140° C).
2. 2,2,2-Trichloroethyl 3-methyl-3-hydroxy-7-(2-phenylacetamido)cepham-4-carboxylate (mp. 169° to 171° C).
3. 2,2,2-Trichloroethyl 3-methyl-3-isopropoxy-7-(2-phenylacetamido)cepham-4-carboxylate (oil).
4. 1-Cyclopropylethyl 3-methyl-3-anilino-7-(2-phenylacetamido)cepham-4-carboxylate (colorless oil).
5. 2,2,2-Trichloroethyl 3-methyl-3-anilino-7-(2-phenylacetamido)cepham-4-carboxylate (oil).
6. 3-anilino-3-methyl-7-(2-phenoxyacetamido)cepham-4-carboxylic acid (mp. 119° to 123° C (dec).

Reaction of:

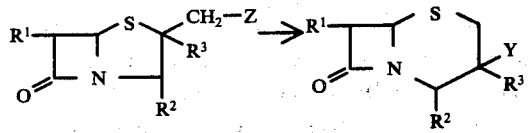

EXAMPLE 1

A mixture of 2,2,2-trichloroethyl 2-bromoethyl-2-methyl-6-(2-phenylacetamido)penam-3-carboxylate (1.08 g), sodium azide (0.26 g), acetone (20 ml) and water (4 ml) was stirred for 4 hours at room temperature. After acetone was distilled off under reduced pressure, the residue was extracted with ethyl acetate. The ethyl acetate layer was washed with water, with saturated sodium bicarbonate aqueous solution and further with water and then dried over magnesium sulfate. The solvent was distilled off under reduced pressure and a small quantity of ether was added to the residue to give colorless crystals of 2,2,2,-trichloroethyl 3-azido-3-methyl-7-(2-phenylacetamido)cepham-4-carboxylate (170 mg). This substance was recrystallized from carbon tetrachloride to give crystals melting at 136° to 140° C.

Infrared Absorption Spectrum (Nujol): 3310, 2110, 1770, 1746, 1658 cm$^{-1}$.

EXAMPLE 2

2,2,2-Trichloroethyl 2-bromomethyl-2-methyl-6-(2-phenylacetamido)penam-3-carboxylate (0.54 g) was dissolved in absolute dimethylsulfoxide (5 ml). To this solution was added silver fluoroborate (0.20 g) and then the mixture was stirred under shielding from light for 3 hours at room temperature. To the solution was added a solution of triethylamine (0.1 g) in dimethylsulfoxide (0.5 ml) and the solution was further stirred for 5 hours and then allowed to stand overnight at room temperature. Precipitates were filtered off and the filtrate was poured into ice-water and then extracted with ethyl acetate. The extract was washed with water and dried. The residue obtained by distilling off the solvent under reduced pressure was crystallized by a small amount of ether to give colorless crystals of 2,2,2-trichloroethyl 3-hydroxy-3-methyl-7-(2-phenylacetamido)cepham-4-carboxylate (280 mg) (58%). This substance was recrystallized from a mixed solvent of benzene-n-hexane to give colorless needles melting at 169° to 171° C.

Analysis for $C_{18}H_{19}N_2O_5SCl_3$: Calc'd: C 44.87, H 3.97, N 5.81, S 6.66, Cl 22.08. Found: C 45.08, H 3.93, N 5.75, S 6.45, Cl 21.96.

EXAMPLE 3

2,2,2-Trichloroethyl 2-bromomethyl-2-methyl-6-(2-phenylacetamido)penam-3-carboxylate (0.55 g) was dissolved in a mixture of tetrahydrofuran (5 ml) and methanol (5 ml). To this solution was added silver fluoroborate (0.24 g) under cooling and then the mixture was stirred for 1 hour. The reaction mixture was concentrated and the obtained residue was dissolved in chloroform. This solution was washed with a saturated sodium bicarbonate aqueous solution and with water and dried over magnesium sulfate. The residue obtained by distilling off the solvent was subjected to chromatography on silica gel using chloroform as developing solvent. The obtained crystals were recrystallized from carbon tetrachloride to give 2,2,2-trichloroethyl 3-methyl-3-methoxy-7-(2-phenylacetamido)-cepham-4-carboxylate (0.27 g), mp. 132° to 133° C.

The similar result was obtained using methylene chloride instead of tetrahydrofuran in the above example.

Infrared Absorption Spectrum (Nujol): 3300, 1780, 1760, 1683 $cm^{-1}$.

EXAMPLE 4

2,2,2-Trichloroethyl 2-bromomethyl-2-methyl-6-(2-phenylacetamido) penam-3-carboxylate (0.55 g) was dissolved in a mixture of tetrahydrofuran (5 ml) and isopropanol (5 ml). To this solution was added silver fluoroborate (0.24 g) under ice-cooling and the mixture was stirred for 1 hour. The reaction mixture was concentrated and the obtained residue was dissolved in chloroform. This solution was washed with a saturated sodium bicarbonate aqueous solution and with water and then dried over magnesium sulfate. The residue obtained by distilling off the solvent was purified by chromatography on silica gel using chloroform as developing solvent to give oily 2,2,2-trichloroethyl 3-methyl-3-isopropoxy-7-(2-phenylacetamido)-cepham-4-carboxylate (0.10 g).

Infrared Absorption Spectrum (Film): 3300, 1760, 1750, 1670 $cm^{-1}$.

EXAMPLE 5

Methyl 2-bromomethyl-2-methyl-6-(2-phenoxyacetamido)penam-3-carboxylate (0.88 g) was dissolved in methylene chloride (13 ml) containing methanol. To the solution was added silver fluoroborate (0.45 g), and the mixture was stirred for 2 hours. After the reaction, the reaction mixture was filtered and the filtrate was washed with a dilute sodium bicarbonate aqueous solution and then with water. The solution was dried over magnesium sulfate and concentrated. The residue was subjected to column chromatography on silica gel (25 g) and eluted with chloroform. The elute was separated into fractions of each about 20 ml and the seventh to tenth fractions were collected. The solvent was distilled off to give Methyl 3-methoxy-3-methyl-7-(2-phenoxyacetamido)cepham-4-carboxylate (0.60 g).

Infrared Absorption Spectrum ($CHCl_3$): 3400, 1772, 1739, 1688 $cm^{-1}$.

The following compounds were obtained by using the same procedures as those of the Examples 1 to 5.
1. Methyl 3-aniline-3-methyl-7-(2-phenoxyacetamido)cepham-4-carboxylate (mp. 129° to 130° C).
2. 1-Cyclopropylethyl 3-anilino-3-methyl-7-(2-phenoxyacetamido)cepham-4-carboxylate (colorless oil).
3. 2,2,2-Trichloroethyl 3-anilino-3-methyl-7-(2-phenoxyacetamido)cepham-4-carboxylate (oil).
4. 3-anilino-3-methyl-7-(2-phenoxyacetamido)-cepham-4-carboxylic acid.

Reaction of:

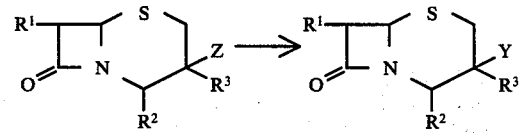

EXAMPLE 1

Anilino (0.28 g) was added to a solution of 2,2,2-trichloroethyl 3-bromo-3-methyl-7-(2-phenylacetamido)-cepham-4-carboxylate (1.10 1 g) in methylene chloride (15 ml). To the solution was added silver fluoborate 0.45 g under ice-cooling under stirring and stirred at the same temperature for 4 hours. After the reaction, the mixture was filtered and the filtrate was washed with dilute phosphoric acid aqueous solution and water in turn. The solution was dried over magnesium sulphate and concentrated. The residue was subjected to column chromatography on silica gel (25 g) using chloroform. The 12th to 13th fractions of fractions, each of which was separated into 20 cc, were concentrated to give oily 2,2,2-trichlocoethyl 3-anilino-3-methyl-7-(2-phenylacetamido)cepham-4-carboxylate.

Infrared Absorption Spectrum ($CHCl_3$): 3420, 1772, 1750, 1680 $cm^{-1}$.

The following compounds were obtained by using the same procedure as that of the Example 1.

| No. | $R^1$ | $R^2$ | $R^3$ | Y | Property of the product |
| --- | --- | --- | --- | --- | --- |
| 1 | ⟨phenyl⟩—$CH_2CONH$— | —$COOCH_2CCl_3$ | —$CH_3$ | —$N_3$ | mp. 136 – 140° C |

-continued

| No. | R¹ | R² | R³ | Y | Property of the product |
|---|---|---|---|---|---|
| 2 | ⌬—CH₂CONH— | —COOCH₂CCl₃ | —CH₃ | —OH | mp. 169 – 171° C |
| 3 | ⌬—CH₂CONH— | —COOCH₂CCl₃ | —CH₃ | —OCH₃ | mp. 132 – 133° C |
| 4 | ⌬—CH₂CONH— | —COOCH₂CCl₃ | —CH₃ | —OCH(CH₃)(CH₃) | oily |
| 5 | ⌬—CH₂CONH— | —COOCH₃ | —CH₃ | —OCH₃ | oily |
| 6 | ⌬—CH₂CONH | —COOCH₃ | —CH₃ | —NH—⌬ | mp. 129 – 130° C |
| 7 | ⌬—CH₂CONH | —COOCH—CH₃ (cyclopropyl) | —CH₃ | —NH—⌬ | colorless oily |
| 8 | ⌬—OCH₂CONH— | —COOH | —CH₃ | —NH—⌬ | mp. 119 – 123° C (dec) |

Reaction of:

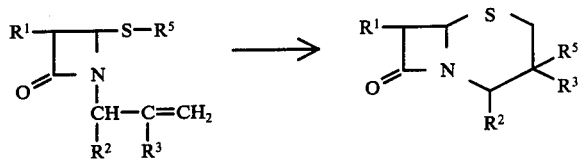

EXAMPLE 1

1-Cyclopropylethyl 2-oxo-3-(2-phenoxyacetamido)-4-anilinothio-α-isopropenyl-1-azetidineacetate (0.4) was dissolved in dried methylene chloride (10 ml). To this solution was added dropwise a solution of boron trifluoride etherate (50 mg) in dried methylene chloride (3 ml) at 0° C and the mixture was stirred for 5 hours at the same temperature. After the reaction, the reaction mixture was washed with 5% sodium bicarbonate aqueous solution and several times with water and then dried. The oil obtained by distilling off the solvent was purified by column chromatography on silica gel using chloroform as developing solvent to give colorless oil of 1-cyclopropylethyl 3-anilino-3-methyl-7-(2-phenoxyacetamido)cepham-4-carboxylate (198 mg.).

Infrared Absorption Spectrum (Film) 3300, 1777, 1740, 1690 cm⁻¹.

EXAMPLE 2

Methyl 2-oxo-3-(2-phenoxyacetamido)-4-anilinothio-α-isopropenyl-1-azetidineacetate (170 mg) was disolved in dried methylene chloride (4 ml). To this solution was added dropwise a solution of boron trifluoride etherate (25 mg) in dried methylene chloride (2 ml) under ice-cooling and the mixture was stirred for 1 hour at the same temperature. After reaction, the reaction mixture was washed with 5% sodium bicarbonate aqueous solution and with water and then dried. The oil obtained by distilling off the solvent was subjected to column chromatography on silica gel using chloroform as developing solvent to give methyl 3-anilino-3-methyl-7-(2-phenoxyacetamido)-cepham-4-carboxylate (80 mg), mp 129° to 130° C, from the fifth to eighth fractions of fractions each of which was separated into 50 ml.

Infrared Absorption Spectrum (CHCl₃) 3420, 1775, 1736, 1691 cm⁻¹.

In the silimar manner, the following compound was obtained.

1. 3-anilino-3-methyl-7-(2-phenoxyacetamido)cepham-4-carboxylic acid (mp 119° to 123° C (dec)).

Reaction of:

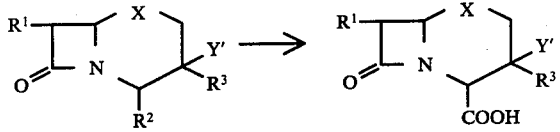

EXAMPLE 1

1-Cyclopropylethyl 3-anilino-3-methyl-7-(2-phenoxyacetamido)-cepham-4-carboxylate (142mg) was dissolved in ice-cooled trifluoroacetic acid (1.5 ml) and the mixture was stirred for 1 hour under ice-cooling. After the reaction, the reaction mixture was concentrated under reduced pressure. The residue was dissolved by adding ethyl acetate and extracted with 5% sodium bicarbonate aqueous solution. The extract was adjusted to pH2 with 5% hydrochloric acid and back-extracted with ethyl acetate. The extract was washed with water, dried and the solvent was distilled off. The residue (amorphous) was dissolved in methanol and to this solution was added water little by little. Precifitates were collected by filtration and dried to give powder of 3-anilino-3-methyl-7-(2-phenoxy-acetamido)cepham-4-carboxylic acid (62 mg), mp 119 to 123° C (dec.).

Analysis for C₂₂H₂₃O₅N₃S. 3/2 H₂O: Calc'd: C 56.40, H 4.95, N 8.97, Found: C 56.57, H 5.05, N 8.97.

IR spectrum (Nujol) 3300, 1770, 1735, 1665 cm⁻¹.

In the similar manner, the following compound was obtained.

1. 3-bromo-3-methyl-7-(2-phenoxy-acetamido)cepham-4-carboxylic acid (amorphous).

Reaction of:

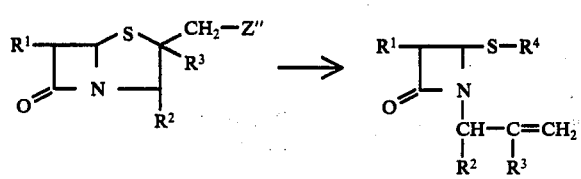

EXAMPLE 1

5-Methyl-1,3,4-thiadiazole-2-thiol (0.16 g) was dissolved in a mixture of pH 6.5 phosphate buffer (5 ml) and acetone (10 ml). To the solution was added 2,2,2-trichloroethyl 2-bromomethyl-2-methyl-6-(2-phenylacetamido)penam-3-carboxylate (0.54 g) and the mixture was stirred for 3 hours at room temperature. The reaction mixture was extracted with ethyl acetate and the ethyl acetate layer was washed with sodium bicarbonate aqueous solution and with water and then dried over magnesium sulfate. The solvent was distilled off from the extract and the residue was purified by column chromatography on silica gel using chloroform as developing solvent to give 2,2,2-trichloroethyl 2-oxo-3-(2-phenylacetamido)-4-(5-methyl-1,3,4-thiadiazol-2-yl)dithio-α-propenyl-1-azetidineacetate (0.24 g), mp 108° to 109° C, from the fifth to ninth fractions of fractions each of which was separated into 30 ml.

Infrared Absorption Spectrum (Nujol): 3280, 1788, 1760, 1654 cm⁻¹.

EXAMPLE 2

2-Mercaptobenzothiazole (0.20 g) was dissolved in a mixture of pH 6.7 phosphate buffer (15 ml) and dioxane (15 ml). To the solution was added 2,2,2-trichloroethyl 2-bromomethyl-2-methyl-6-(2-phenylacetamido)-penam-3-carboxylate (0.54 g) and the mixture was stirred for 7 hours at room temperature. Dioxane was distilled off from the mixture and the residue was extracted with ethyl acetate. The ethyl acetate layer was washed with 2% potassium carbonate aqueous solution and with water and then dried over magnesium sulfate. The residue obtained by distilling off the solvent was purified by column chromatography on silica gel using chloroform as developing solvent to give 2,2,2-trichloroethyl 2-oxo-3-(2-phenylacetamido)-4-(benzothiazol-2-yl)dithio-α-propenyl-1-azetidineacetate (0.10 g), mp 140° to 141° C, from the fourth to sixth fractions of fractions each of which was separated into 30 ml.

EXAMPLE 3

5-Methyl-1,3-thiadiazole-2-thiol (0.4 g) was dissolved in a mixture of pH 7.3 phosphate buffer (20 ml) and acetone (20 ml). To the solution was added a solution of methyl 2-bromomethyl-2-methyl-6-(2-phenoxyacetamido)penam-3-carboxylate (0.80 g) in acetone (10 ml) and the mixture was stirred for 4 hours at room temperature. After the reaction was completed, acetone was distilled off from the reaction mixture and the residue was extracted with ethyl acetate. The extract was washed with sodium bicarbonate aqueous solution and with water, dried over magnesium sulfate and then the solvent was distilled off. The residue was subjected to column chromatography on silica gel (60 g) and eluted with chloroform. The eluate was separated into about 30 ml fraction to give oily methyl 2-oxo-3-(2phenoxyacetamido)-4-(5-methyl-1,3,4-thiadiazol-2-yl)dithio-α-propenyl-1 -azetidineacetate (0.22 g) from the eleventh to thirteenth fractions.

Inferred Absorption Sprectrum (Chloroform): 3430, 1779, 1742, 1692 cm⁻¹.

Further, oily 4,4-dithiobis[methyl-2-oxo-3-(2-phenoxyacetamido)-α-propenyl-1-azetidineacetate] (0.30 g) was obtained from the eighth to tenth fractions of the above fractions.

Infrared Absorption Spectrum (Film) 3280, 1770, 1740, 1680 cm⁻¹.

The following compounds were obtained by using the same procedures as those of the Examples 1 to 3.

| No. | $R^1$ | $R^2$ | $R^3$ | $R^4$ | Property of the product |
|---|---|---|---|---|---|
| 1 | ⟨phenyl⟩-OCH₂CONH— | —COOH | —CH₃ | —S—(N-N, S, CH₃) | mp 142 to 144° C |
| 2 | ⟨phenyl⟩-CH₂CONH— | —COOCH₂CCl₃ | " | " | mp 108 to 109° C |
| 3 | ⟨phenyl⟩-OCH₂CONH— | —COOCH₃ | " | —S—(benzothiazolyl) | mp 146 to 147 ° C |
| 4 | " | —COOH | " | " | mp 146 to 148° C (dec.) |
| 5 | " | —COOCH₂CCl₃ | " | " | mp 171 to 174.5° C |
| 6 | ⟨phenyl⟩-CHCONH—, NH, COOCH₂CCl₃ | —COOCH₂CCl₃ | " | " | mp 159 to 161° C |
| 7 | ⟨phenyl⟩-OCH₂CONH— | —COOH=C(CH₃)(CH₃) | " | " | Oil |
| 8 | ⟨phenyl⟩-CH₂CONH— | —COCH | " | " | mp 76 to 80° C |

-continued $$\begin{array}{c} R^1 \diagdown \phantom{xxx} S-R^4 \\ \phantom{xx}C=O \phantom{xx} N \\ \phantom{xxxxx} CH-C=CH_2 \\ \phantom{xxxxxx} R^2 \phantom{x} R^3 \end{array}$$

| No. | R¹ | R² | R³ | R⁴ | Property of the product |
|---|---|---|---|---|---|
| 9 | " | −COOCH−CH(−CH₂−CH₂ cyclopropyl)−CH₃ | " | " | mp 114 to 117° C |
| 10 | Ph−CHCONH− with NH−COOC(CH₃)₃ | −COOCH₂CCl₃ | " | " | Amorphous |
| 11 | C₂H₅OCOCH=C(CH₃)−NH− | −COOCH₂CCl₃ | " | " | Oil |
| 12 | (isoxazoline)−N−CH₂CONH− | " | " | " | Amorphous |
| 13 | (thiophene-S)−CH₂CONH− | " | " | " | mp 136 to 137° C |
| 14 | Ph−CHCONH− with NH−COOCH(CH₃)−CH(−CH₂−CH₂ cyclopropyl) | " | " | " | mp 164 to 165° C |
| 15 | NCCH₂CONH− | " | " | " | mp 117 to 119° C |
| 16 | Ph−CH₂CONH− | −COOCH₂−(2,6-di-t-C₄H₉-4-OH-phenyl) | " | " | mp 149 to 152° C |
| 17 | HO−C₆H₄−CHCONH− with NH−COOCH(CH₃)−CH(−CH₂−CH₂ cyclopropyl) | −COOCH₂CCl₃ | " | " | mp 175 to 176° C |
| 18 | Ph−OCH₂CONH− | −COOCH−CH(−CH₂−CH₂ cyclopropyl)−CH₃ | " | " | mp 127 to 129° C |
| 19 | " | −COOCH₃ | " | −S−CH₂−Ph | Oil |
| 20 | Ph−OCH₂CONH− | −COOCH₃ | " | −S−COCH₃ | Oil |
| 21 | " | " | " | −S−Ph | Oil |
| 22 | " | " | " | −S−(thiazole) | Oil |
| 23 | " | " | " | −S−(quinoline-2-yl) | Oil |
| 24 | Ph−CH₂CONH− | −COOCH₂CCl₃ | " | −S−(benzoxazol-2-yl) | Oil |

What is claimed is:
1. A compound of the general formula:

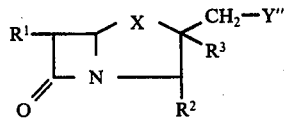

wherein R¹ is a conventional, pharmaceutically acceptable acylamino, R² is carboxy or a conventionally protected carboxy, X is —S— or

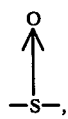

R³ is lower alkyl and Y" is arylamino.

2. The compound according to claim 1, in which R¹ is phenyl(lower)alkanoylamino, phenoxy(lower)alkanoylamino, N-lower alkoxycarbonylphenylglycIamino or 3-halophenyl-5-(lower)alkylisoxazol-4-ylcarboxamido, R² is carboxy, lower alkoxycarbonyl, trihalo(lower)alkoxycarbonyl or carboxy salt, R³ is lower alkyl, X is —S— or

and Y" is anilino.

3. The compound according to claim 1, in which R¹ is phenylacetamido, phenoxyacetamido, N-(1-cyclopropylethoxy)carbonylphenylglycylamino or 3-(2-chlorophenyl)-5-methylisoxazol-4-ylcarboxamido, R² is carboxy, methoxycarbonyl, 2,2,2-trichloroethoxycarbonyl or a carboxy salt with N,N'-dibenzylethylenediamine, R³ is a methyl, X is —S— or

Y"is anilino.

4. The compound according to claim 1, which is 2-anilinomethyl-2-methyl-6-(2-phenylacetamido)penam-3-carboxylic acid.

5. The compound according to claim 1, which is methyl 2-anilinomethyl-2-methyl-6-(2-phenoxyacetamido)penam-3-carboxylate.

6. The compound according to claim 1, which is 2,2,2-trichloroethyl 2-anilinomethyl-2-methyl-6-(2-phenylacetamido)penam-3-carboxylate.

* * * * *